United States Patent
Miyata et al.

(10) Patent No.: US 7,449,325 B2
(45) Date of Patent: Nov. 11, 2008

(54) PROCESS FOR ENZYMATICALLY PRODUCING EITHER OPTICALLY ACTIVE N-SUBSTITUTED β-AMINO ACIDS OR ESTERS THEREOF OR OPTICALLY ACTIVE N-SUBSTITUTED 2-HOMOPIPECOLIC ACIDS OR ESTERS THEREOF

(75) Inventors: Hiroyuki Miyata, Ube (JP); Yasuhito Yamamoto, Ube (JP); Tadayoshi Konegawa, Ube (JP); Kazuma Sakata, Ube (JP)

(73) Assignee: Ube Industries, Ltd., Ube-Shi (JP)

( * ) Notice: Subject to any disclaimer, the term of this patent is extended or adjusted under 35 U.S.C. 154(b) by 431 days.

(21) Appl. No.: 10/510,483

(22) PCT Filed: Apr. 8, 2003

(86) PCT No.: PCT/JP03/04437

§ 371 (c)(1),
(2), (4) Date: Oct. 7, 2004

(87) PCT Pub. No.: WO03/085120

PCT Pub. Date: Oct. 16, 2003

(65) Prior Publication Data

US 2005/0170473 A1    Aug. 4, 2005

(30) Foreign Application Priority Data

Apr. 8, 2002  (JP) ............... 2002-105021
Jun. 13, 2002  (JP) ............... 2002-172678

(51) Int. Cl.
    C12P 41/00    (2006.01)
    C12P 13/04    (2006.01)
(52) U.S. Cl. ..................... 435/280; 435/106
(58) Field of Classification Search ................ 435/106, 435/280
    See application file for complete search history.

(56) References Cited

U.S. PATENT DOCUMENTS 5,928,933 A    7/1999  Dicosimo et al.

FOREIGN PATENT DOCUMENTS

| EP | 0 144 980 A1 | 6/1985 |
| JP | 10-33191 A | 2/1998 |
| WO | WO-95/18134 A1 | 7/1995 |

OTHER PUBLICATIONS

Shun-Ichi Murahashi et al., "A Novel Oxidative Ring-Opening of Isoxazolidiens: Synthesis of Beta-Amino Acid Esters From Secondary Amines", Tetrahedron Letters, 1988, vol. 29 (49), pp. 5949 to 5952.

Primary Examiner—Irene Marx
Assistant Examiner—Susan Hanley
(74) Attorney, Agent, or Firm—Birch, Stewart, Kolasch & Birch, LLP

(57) ABSTRACT

The present invention discloses a process which comprises selectively hydrolyzing one enantiomer of racemic mixtures of an N-substituted β-amino acid alkyl ester or N-substituted 2-homopipecolic acid ester represented by the formula (I):

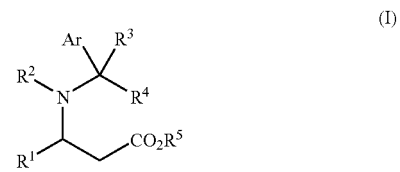

wherein Ar, $R^1$, $R^2$, $R^3$, $R^4$ and $R^5$ are the same as defined in the specification, in the presence of a hydrolase to form an optically active ((R) or (S))—N-substituted β-amino acid or optically active ((R) or (S))—N-substituted 2-homopipecolic acid represented by the formula (II):

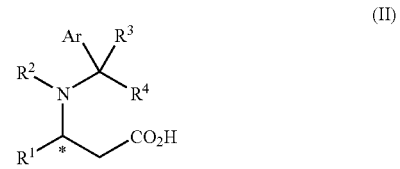

and simultaneously to obtain an unreacted optically active ((S) or (R))—N-substituted β-amino acid alkyl ester or unreacted optically active ((S) or (R))—N-substituted 2-homopipecolic acid ester represented by the formula (III):

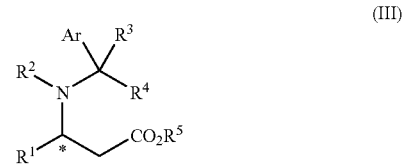

which has a reverse steric absolute configuration to that of the compound represented by the formula (II).

8 Claims, No Drawings

PROCESS FOR ENZYMATICALLY PRODUCING EITHER OPTICALLY ACTIVE N-SUBSTITUTED β-AMINO ACIDS OR ESTERS THEREOF OR OPTICALLY ACTIVE N-SUBSTITUTED 2-HOMOPIPECOLIC ACIDS OR ESTERS THEREOF

This application is a 35 USC 371 national stage application of international application PCT/JP03/04437, filed Apr. 8, 2003, ibr which priority is claimed pursuant to 35 USC 119 based on Japanese application 2002-105021, filed Apr. 8, 2002, and Japanese application 2002-172678, flied Jun. 13. 2002.

TECHNICAL FIELD

The present invention relates to a process for preparing either an optically active ((R) or (S))—N-substituted β-amino acid and an optically active ((S) or (R))—N-substituted β-amino acid alkyl ester or an optically active ((R) or (S))—N-substituted 2-homopipecolic acid and an optically active ((S) or (R))—N-substituted 2-homopipecolic acid ester, simultaneously, from an N-substituted β-amino acid alkyl ester or an N-substituted 2-homopipecolic acid ester (racemic mixture).

Of these, the optically active N-substituted β-amino acid and an ester thereof can be easily introduced into an optically active β-amino acid and an ester thereof which is useful as a synthetic intermediate for a physiologically active peptide or a lactam type antibiotic according to the conventionally known reducing method (for example, Current Medicinal Chemistry, 6, 955 (1999)). Also, of these, the optically active N-substituted 2-homopipecolic acid and an ester thereof can be easily introduced into an optically active 2-homopipecolic acid and an ester thereof which is useful as a synthetic intermediate for a medicine according to the conventionally known reducing method (mentioned in Example 14 below).

BACKGROUND ART

In the prior art, as a method for preparing optically active ((R) or (S))-β-amino acids and optically active ((S) or (R))-β-amino acid esters simultaneously from β-amino acid esters (racemic mixture) by using a hydrolase, it has been disclosed a method in which one of enantiomers of ethyl 3-benzyloxycarbonylaminobutanoate (racemic mixture) is selectively hydrolyzed in 1,4-dioxane to obtain an optically active 3-(S)-aminobutanoic acid ethyl ester and an optically active 3-(R)-aminobutanoic acid in the presence of a lipase originated from *Candida antarctica*, water and triethylamine (Tetrahedron Asymmetry, 8, 37 (1997)).

However, according to this method, there are problems that a reaction time is quite long, an equal amount of triethylamine to the substrate must be added as a third component to heighten optical purity of the object, and the like, and it is disadvantageous as an industrial preparation method.

Also, there is no description about hydrolysis of β-amino acid alkyl esters in which a substituent on a nitrogen atom is an aralkyl group according to the present invention.

Moreover, in the prior art, as a method for preparing an optically active ((R) or (S))—N-substituted 2-homopipecolic acid and an optically active ((S) or (R))—N-substituted 2-homopipecolic acid ester simultaneously from an N-substituted 2-homopipecolic acid ester (racemic mixture) by using a hydrolase, it has been disclosed a method in which one of enantiomers of methyl N-acetyl-2-homopipecolate (racemic mixture) is selectively hydrolyzed in the presence of a Pig liver esterase to obtain an optically active ((R) or (S))—N-acetyl-2-homopipecolic acid and an optically active ((S) or (R))—N-acetyl-2-homopipecolic acid ester (Can. J. Chem., 65, 2722 (1987)).

However, according to this method, there are problems that an amount of the hydrolase to be used is extremely large, optical purity of the objective material is low, and the like, and it is disadvantageous as an industrial preparation method.

An object of the present invention is to solve the above-mentioned problems and to provide a process for preparing an optically active β-amino acid and an optically active β-amino acid ester that is industrially advantageous in which an optically active ((R) or (S))—N-substituted β-amino acid and an optically active ((S) or (R))—N-substituted β-amino acid alkyl ester are obtained simultaneously with high yield and high selectivity from an N-substituted β-amino acid alkyl ester (racemic mixture) according to a simple and easy method.

Another object of the present invention is to solve the above-mentioned problems and to provide a process for preparing an optically active homopipecolic acid and an optically active homopipecolic acid ester that is industrially suitable in which an optically active ((R) or (S))—N-substituted 2-homopipecolic acid and an optically active ((S) or (R))—N-substituted 2-homopipecolic acid ester are obtained simultaneously with high yield and high selectivity from an N-substituted 2-homopipecolic acid ester (racemic mixture).

SUMMARY OF THE INVENTION

An object of the present invention can be solved by a process for preparing an optically active N-substituted β-amino acid and an optically active N-substituted β-amino acid ester, or an optically active N-substituted 2-homopipecolic acid and an optically active N-substituted 2-homopipecolic acid ester which comprises selectively hydrolyzing an enantiomer of an N-substituted β-amino acid alkyl ester or an N-substituted 2-homopipecolic acid ester (racemic mixture) represented by the formula (I):

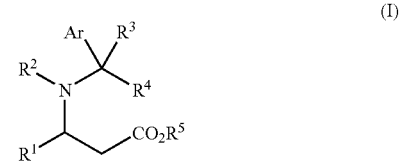

wherein Ar represents a substituted or unsubstituted aryl group, $R^1$ represents a substituted or unsubstituted alkyl group, an alkenyl group, a substituted or unsubstituted aralkyl group or a substituted or unsubstituted aryl group, $R^2$ represents a hydrogen atom, $R^3$ and $R^4$ each independently represent a hydrogen atom, a substituted or unsubstituted alkyl group or a substituted or unsubstituted aryl group, $R^5$ represents a substituted or unsubstituted alkyl group, and $R^1$ and $R^2$ may form a ring by bonding to each other, in the presence of a hydrolase to form an optically active ((R) or (S))—N-substituted β-amino acid or an optically active ((R) or (S))—N-substituted 2-homopipecolic acid represented by the formula (II):

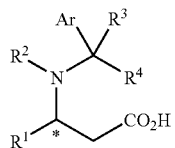

(II)

wherein Ar, $R^1$, $R^2$, $R^3$ and $R^4$ have the same meanings as defined above, and simultaneously to obtain an optically active ((S) or (R))—N-substituted β-amino acid alkyl ester or an optically active ((S) or (R))—N-substituted 2-homopipecolic acid ester (incidentally, it has a reverse steric absolute configuration to that of the compound represented by the formula (II).) represented by the formula (III):

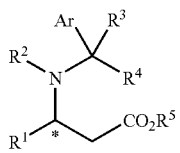

(III)

wherein Ar, $R^1$, $R^2$, $R^3$, $R^4$ and $R^5$ have the same meanings as defined above.

BEST MODE FOR CARRYING OUT THE INVENTION

In the preparation processes of the present inventtion, an N-substituted β-amino acid alkyl ester represented by the following formula (I-a):

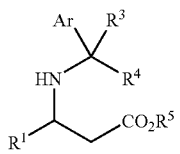

(I-a)

wherein Ar, $R^1$, $R^2$, $R^3$, $R^4$ and $R^5$ have the same meanings as defined above, or an N-substituted 2-homopipecolic acid ester represented by the following formula (I-b):

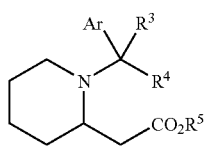

(I-b)

wherein Ar, $R^3$, $R^4$ and $R^5$ have the same meanings as defined above, is used as a representative compound.

In the hydrolysis reaction of the present invention, for example, as shown by the following reaction scheme:

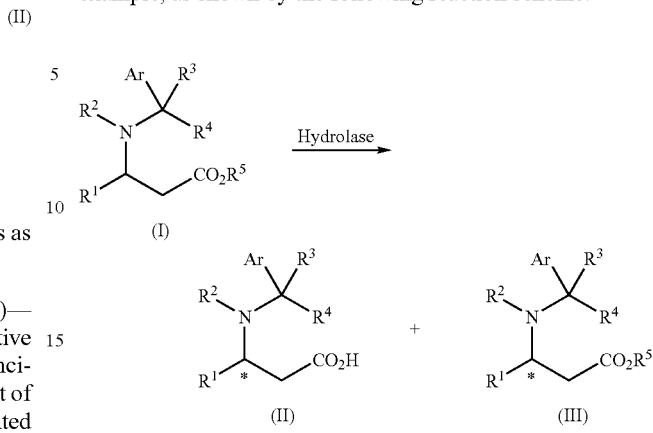

wherein Ar, $R^1$, $R^2$, $R^3$ and $R^4$ have the same meanings as defined above. Incidentally, (II) and (III) have the reverse steric absolute configration to each other, one enantiomer of the racemic mixture (hereinafter sometimes referred to as Compound (I).) of the N-substituted β-amino acid alkyl ester or the N-substituted 2-homopipecolic acid ester represented by the above-mentioned formula (I) is selectively hydrolyzed in the presence of a hydrolase to form an optically active ((R) or (S))—N-substituted β-amino acid or an optically active ((R) or (S))—N-substituted 2-homopipecolic acid ester (hereinafter sometimes referred to as Compound (II).) represented by the formula (II), and simultaneously to obtain an unreacted optically active ((S) or (R))—N-substituted β-amino acid alkyl ester or optically active ((S) or (R))—N-substituted 2-homopipecolic acid ester (hereinafter sometimes referred to as Compound (III).) represented by the formula (III). Incidentally, Compound (II) and Compound (III) have reverse steric absolute configration to each other.

When the N-substituted β-amino acid alkyl ester represented by the above-mentioned formula (I-a) is used, an optically active ((R) or (S))—N-substituted β-amino acid and an optically active ((S) or (R))—N-substituted β-amino acid alkyl ester represented by the following formulae (II-a) and (III-a):

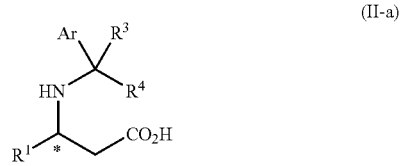

(II-a)

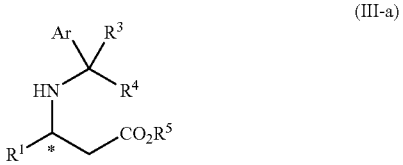

(III-a)

wherein Ar, $R^1$, $R^3$, $R^4$ and $R^5$ have the same meanings as defined above, can be obtained, and when the N-substituted 2-homopipecolic acid ester represented by the above-mentioned formula (I-b) is used, an optically active ((R) or (S))—N-substituted 2-homopipecolic acid and an optically active ((S) or (R))—N-substituted 2-homopipecolic acid ester represented by the following formulae (II-b) and (III-b):

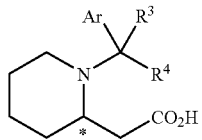
(II-b)

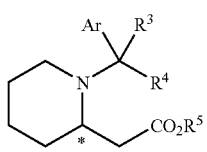
(III-b)

wherein Ar, $R^3$, $R^4$ and $R^5$ have the same meanings as defined above, can be obtained.

Incidentally, in the above-mentioned formulae (II-a) and (III-a), it is particularly preferred that the optically active ((R) or (S))—N-substituted β-amino acid represented by the formula (II-a) is an optically active N-substituted β-amino acid represented by the formula (IV-a):

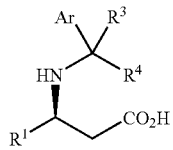
(IV-a)

wherein Ar, $R^3$ and $R^4$ have the same meanings as defined above, and the unreacted optically active ((S) or (R))—N-substituted 2-β-amino acid ester is an optically active N-substituted β-amino acid ester represented by the formula (V-a):

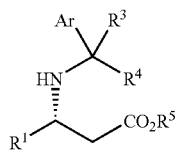
(V-a)

wherein Ar, $R^3$, $R^4$ and $R^5$ have the same meanings as defined above.

Also, in the above-mentioned formulae (II-b) and (III-b), it is particularly preferred that the optically active ((R) or (S))—N-substituted 2-homopipecolic acid represented by the formula (II-b) is an optically active (R)—N-substituted 2-homopipecolic acid represented by the formula (IV-b):

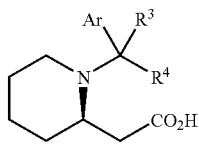
(IV-b)

wherein Ar, $R^3$ and $R^4$ have the same meanings as defined above, and an unreacted optically active ((S) or (R))—N-substituted 2-homopipecolic acid ester is an optically active (S)—N-substituted 2-homopipecolic acid ester represented by the formula (V-b):

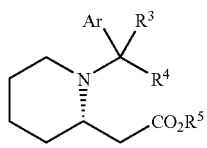
(V-b)

wherein Ar, $R^3$, $R^4$ and $R^5$ have the same meanings as defined above.

In the following, the respective substituents of the compounds of the present invention are explained.

Ar in Compound (I) represents a substituted or unsubstituted aryl group.

The above-mentioned substituted or unsubstituted aryl group is (1) "an aryl group having no substituent" or (2) "an aryl group having a substituent(s)". As "the aryl group having no substituent" of (1), there may be specifically mentioned an aryl group such as a phenyl group, a naphthyl group, an anthryl group, etc. (incidentally, these groups include various kinds of isomers), preferably a phenyl group, a 1-naphthyl group, a 2-naphthyl group. As the substituent(s) for "the aryl group having a substituent(s)" of (2), there may be mentioned, for example, an alkyl group having 1 to 4 carbon atoms such as a methyl group, an ethyl group, a propyl group, a butyl group (incidentally, these groups include various kinds of isomers); a hydroxyl group; a halogen atom such as a fluorine atom, a chlorine atom, a bromine atom, an iodine atom, etc.; an alkoxy group having 1 to 4 carbon atoms such as a methoxy group, an ethoxy group, a propoxy group, a butoxy group, etc. (incidentally, these groups include various kinds of isomers); a nitro group, etc. As the aryl group having such a substituent(s), there may be specifically mentioned a 2-tolyl group, a 3-tolyl group, a 4-tolyl group, a 2,3-xylyl group, a 2,6-xylyl group, a 2,4-xylyl group, a 3,4-xylyl group, a mesityl group, a 2-hydroxyphenyl group, a 4-hydroxyphenyl group, a 3,4-dihydroxyphenyl group, a 2-fluorophenyl group, a 4-fluorophenyl group, a 2-chlorophenyl group, a 3-chlorophenyl group, a 4-chlorophenyl group, a 3,4-dichlorophenyl group, a 4-bromophenyl group, a 4-iodophenyl group, a 2-methoxyphenyl group, a 3-methoxyphenyl group, a 4-methoxyphenyl group, a 3,4-dimethoxyphenyl group, a 3,4-methylenedioxyphenyl group, a 4-ethoxyphenyl group, a 4-butoxy phenyl group, a 4-isopropoxyphenyl group, a 4-nitrophenyl group, a 2-nitrophenyl group, etc., preferably a 2-tolyl group, a 4-tolyl group, a 2,3-xylyl group, a 3,4-xylyl group, a 4-hydroxyphenyl group, a 3,4-dihydroxyphenyl group, a 2-fluorophenyl group, a 4-fluorophenyl group, a 2-chlorophenyl group, a 4-chlorophenyl group, a 3,4-dichlorophenyl group, a 2-methoxyphenyl group, a 4-methoxyphenyl group, a 3,4-dimethoxyphenyl group, a 3,4-methylenedioxyphenyl group, a 4-ethoxyphenyl group, a 4-nitrophenyl group, a 2-nitrophenyl group, more preferably a 4-tolyl group, a 4-hydroxyphenyl group, a 3,4-dihydroxyphenyl group, a 4-fluorophenyl group, a 4-chlorophenyl group, a 4-methoxyphenyl group, a 3,4-dimethoxyphenyl group, a 3,4-methylenedioxyphenyl group and a 4-nitrophenyl group.

$R^1$ of Compound (I) represents a substituted or unsubstituted alkyl group, alkenyl group, a substituted or unsubstituted aralkyl group or a substituted or unsubstituted aryl group.

The above-mentioned substituted or unsubstituted alkyl group means (3) "an alkyl group having no substituent" or (4) "an aryl group having a substituent(s)". As "the alkyl group having no substituent" of (3), there may be mentioned, more specifically, an alkyl group having 1 to 10 carbon atoms such as a methyl group, an ethyl group, a propyl group, a butyl group, a pentyl group, a hexyl group, a heptyl group, an octyl group, a nonyl group, decyl group, etc (incidentally, these groups include various kinds of isomers), preferably a methyl group, an ethyl group, a n-propyl group, an isopropyl group, a n-butyl group, a n-octyl group, more preferably a methyl group, an ethyl group. As the substituent for (4) "the alkyl group having a substituent(s)", there may be mentioned, for example, a halogen atom such as a fluorine atom, a chlorine atom, a bromine atom, an iodine atom, etc.; a hydroxyl group; an alkoxyl group having 1 to 4 carbon atoms such as a methoxyl group, an ethoxyl group, a propoxyl group, a butoxyl group, etc. (incidentally, these groups include various kinds of isomers); an amino group; a dialkylamino group such as a dimethylamino group, a diethylamino group, a dipropylamino group, etc. (incidentally, these groups include various kinds of isomers); a cyano group; a nitro group, etc., preferably a fluorine atom, a chlorine atom, a hydroxyl group, an amino group, a dimethylamino group, a diethylamino group, a cyano group. As the alkyl group having such a substituent, there may be mentioned, more specifically, a fluoromethyl group, a chloromethyl group, a hydroxymethyl group, a methoxymethyl group, an aminomethyl group, a dimethylaminomethyl group, a 2-chloroethyl group, a 2,2-dichloroethyl group, a 2,2,2-trichloroethyl-group, a 2,2,2-trifluoroethyl group, a 2-hydroxyethyl group, a 2-cyanoethyl group, a 2-methoxyethyl group, a 2-ethoxyethyl group, a 2-bromoethyl group, a 2-dimethylamino group, a 2-chloropropyl group, a 3-chloropropyl group, etc., preferably a fluoromethyl group, a chloromethyl group, a hydroxymethyl group, an aminomethyl group, a dimethylaminomethyl group, a 2-chloroethyl group, a 2,2,2-trichloroethyl group, a 2,2,2-trifluoroethyl group, and a 2-cyanoethyl group.

The above-mentioned alkenyl group of $R^1$ may be mentioned, specifically an alkenyl group having 2 to 10 carbon atoms such as a vinyl group, a propenyl group, a butenyl group, a pentenyl group, a hexenyl group, a heptenyl group, an octenyl group, a nonenyl group, a decenyl group, etc. (incidentally, these groups include various kinds of isomers), preferably a vinyl group, a propenyl group, a butenyl group, a pentenyl group, more preferably a vinyl group, a 1-propenyl group, and a 2-propenyl group.

The substituted or unsubstituted aralkyl group of the above-mentioned $R^1$ is (5) "an aralkyl group having no substituent" or (6) "an aralkyl group having a substituent(s)". "The aralkyl group having no substituent" of (5) may be mentioned, more specifically, an aralkyl group (incidentally, these groups include various kinds of isomers) such as a benzyl group, a phenethyl group, a phenylpropyl group, a phenylbutyl group, etc., preferably a benzyl group, a 1-phenethyl group, a 2-phenethyl group, a 3-phenylpropyl group, a 3-phenylbutyl group. As the substituent for "the aralkyl group having a substituent(s)" of (6), there may be mentioned, for example, an alkyl group having 1 to 10 carbon atoms such as a methyl group, an ethyl group, a propyl group, a butyl group, a pentyl group, a hexyl group, a heptyl group, an octyl group, a nonyl group, a decyl group, etc. (incidentally, these groups include various kinds of isomers); a hydroxyl group; a nitro group; a halogen atom such as a fluorine atom, a chlorine atom, a bromine atom, an iodine atom, etc.; an alkoxy group having 1 to 10 carbon atoms such as a methoxy group, an ethoxy group, a propoxy group, a butoxy group, a pentyloxy group, a hexyloxy group, a heptyloxy group, an octyloxy group, a nonyloxy group, a decyloxy group (incidentally, these groups include various kinds of isomers); an aralkyloxy group having 7 to 10 carbon atoms such as a benzyloxy group, a phenethyloxy group, a phenylpropoxy group (incidentally, these groups include various kinds of isomers); an aryloxy group such as a phenyloxy group, naphthyloxy group, etc. (incidentally, these groups include various kinds of isomers); an alkoxyalkoxy group such as a methoxymethoxy group, a methoxyethoxy group, etc. (incidentally, these groups include various kinds of isomers); a monoalkylamino group such as a methylamino group, an ethylamino group, etc. (incidentally, these groups include various kinds of isomers); a dialkylamino group such as a dimethylamino group, a diethylamino group, etc. (incidentally, these groups include various kinds of isomers); an acylamino group such as a formylamino group, an acetylamino group, a benzoylamino group, etc. (incidentally, these groups include various kinds of isomers), a nitro group, a cyano group, a trifluoromethyl group, and the like. The aralkyl group having such a substituent(s) may be mentioned, more specifically, a 2-fluorobenzyl group, a 3-fluorobenzyl group, a 4-fluorobenzyl group, a 3,4-difluorobenzyl group, a 2,4-difluorobenzyl group, a 2-chlorobenzyl group, a 3-chlorobenzyl group, a 4-chlorobenzyl group, a 2,4-dichlorobenzyl group, a 3,4-dichlorobenzyl group, a 2-bromobenzyl group, a 3-bromobenzyl group, a 4-bromobenzyl group, a 2,4-dibromobenzyl group, a 3,4-dibromobenzyl group, a 2-iodobenzyl group, a 3-iodobenzyl group, a 4-iodobenzyl group, a 2,3-diiodobenzyl group, a 3,4-diiodobenzyl group, a 2-methylbenzyl group, a 3-methylbenzyl group, a 4-methylbenzyl group, a 2-ethylbenzyl group, a 3-ethylbenzyl group, a 4-ethylbenzyl group, a 2-hydroxybenzyl group, a 3-hydroxybenzyl group, a 4-hydroxybenzyl group, a 2-methoxybenzyl group, a 3-methoxybenzyl group, a 4-methoxybenzyl group, a 2,4-dimethoxybenzyl group, a 3,4-dimethoxybenzyl group, a 2-ethoxybenzyl group, a 4-ethoxybenzyl group, a 2-trifluoromethylbenzyl group, a 4-trifluoromethylbenzyl group, a 4-benzyloxybenzyl group, a 2-nitrobenzyl group, a 3-nitrobenzyl group, a 4-nitrobenzyl group, a 2-cyanobenzyl group, a 3-cyanobenzyl group, a 4-cyanobenzyl group, a 4-dimethylaminobenzyl group, a 4-formylaminobenzyl group, a 2-acetylaminobenzyl group, a 3-acetylaminobenzyl group, a 4-acetylaminobenzyl group, a 4-benzoylaminobenzyl group, a 2-(2-fluorophenyl)ethyl group, a 2-(3-fluorophenyl)ethyl group, a 2-(4-fluorophenyl)ethyl group, a 2-(3,4-difluorophenyl)ethyl group, a 2-(2,4-difluorophenyl)ethyl group, a 2-(2-chlorophenyl)ethyl group, a 2-(3-chlorophenyl)ethyl group, a 2-(4-chlorophenyl)ethyl group, a 2-(2,4-dichlorophenyl)ethyl group, a 2-(3,4-dichlorophenyl)ethyl group, a 2-(2-bromophenyl)

ethyl group, a 2-(3-bromophenyl)ethyl group, a 2-(4-bromophenyl)ethyl group, a 2-(2,4-dibromophenyl)ethyl group, a 2-(3,4-dibromophenyl)ethyl group, a 2-(2-iodophenyl)ethyl group, a 2-(3-iodophenyl)ethyl group, a 2-(4-iodophenyl)ethyl group, a 2-(2,3-diiodophenyl)ethyl group, a 2-(3,4-diiodophenyl)ethyl group, a 2-(2-tolyl)ethyl group, a 2-(3-tolyl)ethyl group, a 2-(4-tolyl)ethyl group, a 2-(2-ethylphenyl)ethyl group, a 2-(3-ethylphenyl)ethyl group, a 2-(4-ethylphenyl)ethyl group, a 2-(2-hydroxyphenyl)ethyl group, a 2-(4-hydroxyphenyl)ethyl group, a 2-(2-methoxyphenyl)ethyl group, a 2-(3-methoxyphenyl)ethyl group, a 2-(4-methoxyphenyl)ethyl group, a 2-(2,4-dimethoxyphenyl)ethyl group, a 2-(3,4-dimethoxyphenyl)ethyl group, a 2-(2-ethoxyphenyl)ethyl group, a 2-(4-ethoxyphenyl)ethyl group, a 2-(2-trifluoromethylphenyl)ethyl group, a 2-(4-trifluoromethylphenyl)ethyl group, a 2-(4-benzyloxyphenyl)ethyl group, a 2-(2-nitrophenyl)ethyl group, a 2-(3-nitrophenyl)ethyl group, a 2-(4-nitrophenyl)ethyl group, a 2-(2-cyanophenyl)ethyl group, a 2-(3-cyanophenyl)ethyl group, a 2-(4-cyanophenyl)ethyl group, a 2-(4-dimethylaminophenyl)ethyl group, a 2-(4-formylaminophenyl)ethyl group, a 2-(2-acetylaminophenyl)ethyl group, a 2-(3-acetylaminophenyl)ethyl group, a 2-(4-acetylaminophenyl)ethyl group, a 2-(4-benzoylaminophenyl)ethyl group, a 3-(2-fluorophenyl)propyl group, a 3-(4-fluorophenyl)propyl group, a 3-(4-chlorophenyl)propyl group, a 3-(4-bromophenyl)propyl group, a 3-(4-iodophenyl)propyl group, a 3-(2-chlorophenyl)propyl group, a 3-(2-methoxyphenyl)propyl group, a 3-(4-methoxyphenyl)propyl group, a 3-(3,4-dimethoxyphenyl)propyl group, a 3-(4-trifluoromethylphenyl)propyl group, a 3-(2-trifluoromethylphenyl)propyl group, a 3-(4-nitrophenyl)propyl group, a 3-(4-cyanophenyl)propyl group, a 3-(4-acetylaminophenyl)propyl group, and the like, preferably a 2-fluorobenzyl group, a 3-fluorobenzyl group, a 4-fluorobenzyl group, a 2-chlorobenzyl group, a 3-chlorobenzyl group, a 4-chlorobenzyl group, a 2-bromobenzyl group, a 3-bromobenzyl group, a 4-bromobenzyl group, a 2-iodobenzyl group, a 3-iodobenzyl group, a 4-iodobenzyl group, a 2-methylbenzyl group, a 3-methylbenzyl group, a 4-methylbenzyl group, a 2-hydroxybenzyl group, a 4-hydroxybenzyl group, a 2-methoxybenzyl group, a 3-methoxybenzyl group, a 4-methoxybenzyl group, a 3,4-dimethoxybenzyl group, a 2-trifluoromethylbenzyl group, a 4-trifluoromethylbenzyl group, a 4-benzyloxybenzyl group, a 2-nitrobenzyl group, a 3-nitrobenzyl group, a 4-nitrobenzyl group, a 2-cyanobenzyl group, a 3-cyanobenzyl group, a 4-cyanobenzyl group, a 4-formylaminobenzyl group, a 3-acetylaminobenzyl group, a 4-acetylaminobenzyl group, a 4-benzoylaminobenzyl group, a 2-(2-fluorophenyl)ethyl group, a 2-(3-fluorophenyl)ethyl group, a 2-(4-fluorophenyl)ethyl group, a 2-(2-chlorophenyl)ethyl group, a 2-(3-chlorophenyl)ethyl group, a 2-(4-chlorophenyl)ethyl group, a 2-(2-bromophenyl)ethyl group, a 2-(3-bromophenyl)ethyl group, a 2-(4-bromophenyl)ethyl group, a 2-(2-iodophenyl)ethyl group, a 2-(3-iodophenyl)ethyl group, a 2-(4-iodophenyl)ethyl group, a 2-(2-tolyl)ethyl group, a 2-(3-tolyl)ethyl group, a 2-(4-tolyl)ethyl group, a 2-(2-ethylphenyl)ethyl group, a 2-(2-hydroxyphenyl)ethyl group, a 2-(4-hydroxyphenyl)ethyl group, a 2-(2-methoxyphenyl)ethyl group, a 2-(3-methoxyphenyl)ethyl group, a 2-(4-methoxyphenyl)ethyl group, a 2-(2,4-dimethoxyphenyl)ethyl group, a 2-(3,4-dimethoxyphenyl)ethyl group, a 2-(2-trifluoromethylphenyl)ethyl group, a 2-(4-trifluoromethylphenyl)ethyl group, a 2-(4-benzyloxyphenyl)ethyl group, a 2-(2-nitrophenyl)ethyl group, a 2-(3-nitrophenyl)ethyl group, a 2-(4-nitrophenyl)ethyl group, a 2-(2-cyanophenyl)ethyl group, a 2-(3-cyanophenyl)ethyl group, a 2-(4-cyanophenyl)ethyl group, a 2-(2-acetylaminophenyl)ethyl group, a 2-(3-acetylaminophenyl)ethyl group, a 2-(4-acetylaminophenyl)ethyl group, a 2-(4-benzoylaminophenyl)ethyl group, a 3-(2-fluorophenyl)propyl group, a 3-(4-fluorophenyl)propyl group, a 3-(4-chlorophenyl)propyl group, a 3-(4-bromophenyl)propyl group, a 3-(4-iodophenyl)propyl group, a 3-(2-chlorophenyl)propyl group, a 3-(2-methoxyphenyl)propyl group, a 3-(4-methoxyphenyl)propyl group, a 3-(3,4-dimethoxyphenyl)propyl group, a 3-(4-trifluoromethylphenyl)propyl group, a 3-(2-trifluoromethylphenyl)propyl group, a 3-(4-nitrophenyl)propyl group, a 3-(4-cyanophenyl)propyl group, a 3-(4-acetylaminophenyl)propyl group, more preferably a 2-fluorobenzyl group, a 4-fluorobenzyl group, a 2-chlorobenzyl group, a 4-chlorobenzyl group, a 2-bromobenzyl group, a 4-bromobenzyl group, a 2-iodobenzyl group, a 4-iodobenzyl group, a 2-methylbenzyl group, a 4-methylbenzyl group, a 4-hydroxybenzyl group, a 2-methoxybenzyl group, a 4-methoxybenzyl group, a 3,4-dimethoxybenzyl group, a 2-trifluoromethylbenzyl group, a 4-trifluoromethylbenzyl group, a 4-benzyloxybenzyl group, a 2-nitrobenzyl group, a 4-nitrobenzyl group, a 2-cyanobenzyl group, a 3-cyanobenzyl group, a 4-cyanobenzyl group, a 3-acetylaminobenzyl group, a 4-acetylaminobenzyl group, a 2-(2-fluorophenyl)ethyl group, a 2-(4-fluorophenyl)ethyl group, a 2-(2-chlorophenyl)ethyl group, a 2-(4-chlorophenyl)ethyl group, a 2-(2-bromophenyl)ethyl group, a 2-(4-bromophenyl)ethyl group, a 2-(2-iodophenyl)ethyl group, a 2-(4-iodophenyl)ethyl group, a 2-(2-tolyl)ethyl group, a 2-(4-tolyl)ethyl group, a 2-(4-hydroxyphenyl)ethyl group, a 2-(2-methoxyphenyl)ethyl group, a 2-(4-methoxyphenyl)ethyl group, a 2-(3,4-dimethoxyphenyl)ethyl group, a 2-(2-trifluoromethylphenyl)ethyl group, a 2-(4-trifluoromethylphenyl)ethyl group, a 2-(4-benzyloxyphenyl)ethyl group, a 2-(2-nitrophenyl)ethyl group, a 2-(4-nitrophenyl)ethyl group, a 2-(2-cyanophenyl)ethyl group, a 2-(4-cyanophenyl)ethyl group, a 2-(2-acetylaminophenyl)ethyl group, a 2-(4-acetylaminophenyl)ethyl group.

The substituted or unsubstituted aryl group of the above-mentioned $R^1$ has the same meanings as that of the substituted or unsubstituted aryl group of the above-mentioned Ar.

$R^2$ of Compound (I) is a hydrogen atom or $R^1$ and $R^2$ may bind to each other to form a ring with atoms to which they are bonded. When $R^2$ is a hydrogen atom, it becomes an N-substituted β-amino acid alkyl ester represented by the formula (I-a). Also, as the case where $R^1$ and $R^2$ bind to form a ring with atoms to which they are bonded, there may be mentioned a case where it forms a $C_3$ to $C_6$ saturated ring, and of these, the case where $R^1$ and $R^2$ forms a $C_4$ saturated alkylene group is particularly preferred. When $R^1$ and $R^2$ bind to form a $C_4$ saturated alkylene group, it becomes an N-substituted 2-homopipecolic acid ester represented by the formula (I-b).

$R^3$ and $R^4$ of the Compound (I) each independently represent a hydrogen atom, a substituted or unsubstituted alkyl group or a substituted or unsubstituted aryl group.

The above-mentioned substituted or unsubstituted alkyl group has the same meanings as that of the substituted or unsubstituted alkyl group of the above-mentioned $R^1$, and the above-mentioned substituted or unsubstituted aryl group has the same meanings as that of the substituted or unsubstituted aryl group of the above-mentioned Ar.

$R^5$ of Compound (I) represents a substituted or unsubstituted alkyl group.

The substituted or unsubstituted alkyl group of the above-mentioned $R^5$ has the same meanings as that of the substituted or unsubstituted alkyl group of the above-mentioned $R^1$.

Compound (I-a) to be used in the hydrolysis reaction of the present invention can be easily synthesized by, for example, subjecting β-keto esters and 1-arylalkylamines to dehydration condensation to form corresponding enamines, and then subjecting the resulting compound to reduction by hydrogen (for example, Current Medicinal Chemistry, 6, 955 (1999)). Also, Compound (I-b) to be used in the hydrolysis reaction of the present invention can be easily synthesized by, for example, oxidizing 2-(2-piperidin)ethanol to synthesize 2-carboxymethylpiperidine (Can. J. Chem., 53, 41 (1975)), then, esterifying the resulting compound to make 2-carbomethoxymethylpiperidine (Can. J. Chem., 65, 2722 (1987)), and further subjecting to benzylation of the resulting compound (described in Reference example 3 mentioned below).

Specific examples of Compound (I-a) having the above-mentioned Ar, $R^1$, $R^3$, $R^4$ and $R^5$ may include, for example,
methyl 3-benzylaminobutyrate,
ethyl 3-benzylaminobutyrate,
n-propyl 3-benzylaminobutyrate,
b-butyl 3-benzylaminobutyrate,
n-octyl 3-benzylaminobutyrate,
2-chloroethyl 3-benzylaminobutyrate,
2,2,2-trichloroethyl 3-benzylaminobutyrate,
2,2,2-trifluoroethyl 3-benzylaminobutyrate,
2-cyanoethyl 3-benzylaminobutyrate,
methyl 3-(4-chlorobenzylamino)butyrate,
methyl 3-(4-fluorobenzylamino)butyrate,
methyl 3-(4-methoxybenzylamino)acetate,
methyl 3-(4-hydroxybenzyl)aminoacetate,
methyl 3-(4-methylbenzyl)aminobutyrate,
methyl 3-(3,4-dimethoxybenzyl)aminobutyrate,
methyl 3-(3,4-methylenedioxybenzyl)aminobutyrate,
methyl 3-(4-nitrobenzyl)aminobutyrate,
methyl 3-(1-naphthylmethyl)aminobutyrate,
methyl 3-(1-phenylethyl)aminobutyrate,
methyl 3-(1-(2-chlorophenyl)ethyl)aminobutyrate,
methyl 3-(1-(1-naphthyl)ethyl)aminobutyrate,
methyl 3-diphenylmethylaminobutyrate,
methyl 3-tritylaminobutyrate,
methyl 3-benzylaminopentanoate,
ethyl 3-benzylaminopentanoate,
2,2,2-trifluoroethyl 3-benzylamino pentanoate,
methyl 3-(4-chlorobenzylamino) pentanoate,
methyl 3-(4-methoxybenzylamino)pentanoate,
ethyl 3-(4-nitrobenzylamino)pentanoate,
methyl 3-benzylaminohexanoate,
ethyl 3-benzylaminohexanoate,
2,2,2-trichloroethyl 3-benzylaminohexanoate,
2,2,2-trifluoroethyl 3-benzylaminohexanoate,
methyl 3-benzylamino-4-methylpentanoate,
ethyl 3-benzylamino-4-methylpentanoate,
n-propyl 3-benzylamino-4-methylpentanoate,
n-butyl 3-benzylamino-4-methylpentanoate,
n-pentyl 3-benzylamino-4-methylpentanoate,
n-octyl 3-benzylamino-4-methylpentanoate,
2-chloroethyl 3-benzylamino-4-methylpentanoate,
2,2,2-trichloroethyl 3-benzylamino-4-methylpentanoate,
2,2,2-trifluoroethyl 3-benzylamino-4-methylpentanoate,
methyl 3-(2-methylbenzyl)-4-methylpentanoate,
methyl 3-(3-methylbenzyl)-4-methylpentanoate,
methyl 3-(4-methylbenzyl)-4-methylpentanoate,
methyl 3-(2-methoxybenzyl)-4-methylpentanoate,
methyl 3-(3-methoxybenzyl)amino-4-methylpentanoate,
methyl 3-(4-methoxybenzyl)amino-4-methylpentanoate,
butyl 3-(2-chlorobenzyl)amino-4-methylpentanoate,
ethyl 3-(3-chlorobenzyl)amino-4-methylpentanoate,
methyl 3-(4-chlorobenzyl)amino-4-methylpentanoate,
methyl 3-(2-bromobenzyl)amino-4-methylpentanoate,
methyl 3-(3-bromobenzyl)amino-4-methylpentanoate,
ethyl 3-(4-bromobenzyl)amino-4-methylpentanoate,
methyl 3-(2-fluorobenzyl)amino-4-methylpentanoate,
methyl 3-(2-nitrobenzyl)amino-4-methylpentanoate,
methyl 3-(4-nitrobenzyl)amino-4-methylpentanoate,
methyl 3-(2-methoxybenzyl)amino-4-methylpentanoate,
methyl 3-(3-methoxybenzyl)amino-4-methylpentanoate,
methyl 3-(4-methoxybenzyl)amino-4-methylpentanoate,
methyl 3-(3,4-dimethoxybenzyl)amino-4-methylpentanoate,
methyl 3-(3,4-methylenedioxybenzyl)amino-4-methylpentanoate,
methyl 3-benzylamino-4-chlorobutyrate,
ethyl 3-benzylamino-4-chlorobutyrate,
methyl 3-benzylamino-4-hydroxybutyrate,
ethyl 3-benzylamino-4-hydroxybutyrate,
methyl 3-benzylamino-3-phenylpropionate,
ethyl 3-benzylamino-3-phenylpropionate,
n-propyl 3-benzylamino-3-phenylpropionate,
n-butyl 3-benzylamino-3-phenylpropionate,
n-octyl 3-benzylamino-3-phenylpropionate,
2-chloroethyl 3-benzylamino-3-phenylpropionate,
2,2,2-trichloroethyl 3-benzylamino-3-phenylpropionate,
2,2,2-trifluoroethyl 3-benzylamino-3-phenylpropionate,
2-cyanoethyl 3-benzylamino-3-phenylpropionate,
methyl 3-(4-methoxybenzylamino)-3-phenylpropionate,
methyl 3-(4-hydroxybenzyl)amino-3-phenylpropionate,
methyl 3-(4-methylbenzyl)amino-3-phenylpropionate,
methyl 3-(3,4-dimethoxybenzyl)amino-3-phenylpropionate,
methyl 3-(3,4-methylenedioxybenzyl)amino-3-phenylpropionate,
methyl 3-(4-nitrobenzyl)amino-3-phenylpropionate,
methyl 3-(1-phenylethyl)amino-3-phenylpropionate,
methyl 3-(1-(1-naphthyl)ethyl)amino-3-phenylpropionate,
methyl 3-diphenylmethylamino-3-phenylpropionate,
methyl 3-tritylamino-3-phenylpropionate,
methyl 3-benzylamino-3-(2-fluorophenyl)propionate,
methyl 3-benzylamino-3-(4-fluorophenyl)propionate,
ethyl 3-benzylamino-3-(4-fluorophenyl)propionate,
methyl 3-diphenylmethylamino-3-(4-fluorophenyl)propionate,
methyl 3-benzylamino-3-(2-chlorophenyl)phenylpropionate,
methyl 3-benzylamino-3-(4-chlorophenyl)phenylpropionate,
methyl 3-benzylamino-3-(4-bromophenyl)propionate,
ethyl 3-benzylamino-3-(4-iodophenyl)propionate,
methyl 3-benzylamino-3-(4-hydroxyphenyl)propionate,
ethyl 3-benzylamino-3-(2-hydroxyphenyl)propionate,
methyl 3-benzylamino-3-(2-methoxyphenyl)propionate,
methyl 3-benzylamino-3-(4-methoxyphenyl)propionate,
ethyl 3-benzylamino-3-(4-methoxyphenyl)propionate,
methyl 3-diphenylmethylamino-3-(4-methoxyphenyl)propionate,
methyl 3-benzylamino-3-(3,4-dimethoxyphenyl)propionate,
ethyl 3-benzylamino-3-(3,4-dimethoxyphenyl)propionate,
methyl 3-diphenylmethylamino-3-(3,4-dimethoxyphenyl)propionate,
methyl 3-benzylamino-3-(3,4-methylenedioxyphenyl)propionate,
ethyl 3-benzylamino-3-(3,4-methylenedioxyphenyl)propionate,
ethyl 3-diphenylmethylamino-3-(3,4-methylenedioxyphenyl)propionate,
methyl 3-benzylamino-3-(4-tolyl)propionate,
ethyl 3-benzylamino-3-(4-tolyl)propionate,
methyl 3-diphenylmethylamino-3-(4-tolyl)propionate,
methyl 3-benzylamino-3-(2-tolyl)propionate, methyl 3-benzylamino-4-phenylbutyrate,
ethyl 3-benzylamino-4-phenylbutyrate,
methyl 3-benzylamino-4-(4-fluorophenyl)butyrate,
methyl 3-benzylamino-4-(2-fluorophenyl)butyrate,
methyl 3-benzylamino-4-(4-chlorophenyl)butyrate,
methyl 3-benzylamino-4-(4-iodophenyl)butyrate,
methyl 3-benzylamino-4-(4-methoxyphenyl)butyrate,
methyl 3-benzylamino-4-(2-methoxyphenyl)butyrate,
methyl 3-benzylamino-4-(3,4-dimethoxyphenyl)butyrate,
methyl 3-benzylamino-4-(4-hydroxyphenyl)butyrate,
methyl 3-benzylamino-5-phenylpentanoate,
methyl 3-benzylamino-5-(4-fluorophenyl)pentanoate,
methyl 3-benzylamino-5-(4-chlorophenyl)pentanoate,
methyl 3-benzylamino-5-(2-fluorophenyl)pentanoate,
methyl 3-benzylamino-5-(4-methoxyphenyl)pentanoate,
methyl 3-benzylamino-5-(2-methoxyphenyl)pentanoate,
methyl 3-benzylamino-5-(3,4-dimethoxyphenyl)pentanoate,
methyl 3-(1-phenylethyl)amino-5-phenylpentanoate,
methyl 3-benzhydrylamino-5-phenylpentanoate,
methyl 3-(1-phenylethyl)amino-4-chlorobutyrate,
ethyl 3-benzhydrylamino-4-hydroxybutyrate,
ethyl 3-(1-phenylethyl)amino-4-hydroxybutyrate,
ethyl 3-benzhydrylamino-4-hydroxybutyrate,
methyl 3-(1-phenylethyl)aminobutyrate,
methyl 3-benzhydrylaminopentanoate,
methyl 3-(1-phenylethyl)amino-4-methylpentanoate,
ethyl 3-benzhydrylamino-4-methylpentanoate,
methyl 3-(1-naphthylmethyl)aminobutyrate,
methyl 3-(2-naphthylmethyl)aminobutyrate,
methyl 3-(2-naphthylmethyl)aminopentanoate,
methyl 3-(2-naphthylmethyl)amino-4-methylpentanoate,
methyl 3-(1-(1-naphthyl)ethylamino-4-methylpentanoate, etc., preferably
methyl 3-benzylaminobutyrate,
ethyl 3-benzylaminobutyrate,
n-octyl 3-benzylaminobutyrate,
2-chloroethyl 3-benzylaminobutyrate,
2,2,2-trichloroethyl 3-benzylaminobutyrate,
2,2,2-trifluoroethyl 3-benzylaminobutyrate,
methyl 3-(4-chlorobenzylamino)butyrate,
methyl 3-(4-fluorobenzylamino)butyrate,
methyl 3-(4-methoxybenzylamino)acetate,
methyl 3-(4-hydroxybenzyl)aminoacetate,
methyl 3-(4-methylbenzyl)aminobutyrate,
methyl 3-(3,4-dimethoxybenzyl)aminobutyrate,
methyl 3-(3,4-methylenedioxybenzyl)aminobutyrate,
methyl 3-(4-nitrobenzyl)aminobutyrate,
methyl 3-(1-naphthylmethyl)aminobutyrate,
methyl 3-(1-phenylethyl)aminobutyrate,
methyl 3-(1-(1-naphthyl)ethyl)aminobutyrate,
methyl 3-diphenylmethylaminobutyrate,
methyl 3-benzylaminopentanoate,
ethyl 3-benzylaminopentanoate,
methyl 3-(4-chlorobenzylamino)pentanoate,
methyl 3-(4-methoxybenzylamino)pentanoate,
ethyl 3-(4-nitrobenzylamino)pentanoate,
methyl 3-benzylaminohexanoate,
ethyl 3-benzylaminohexanoate,
2,2,2-trifluoroethyl 3-benzylaminohexanoate,
methyl 3-benzylamino-4-methylpentanoate,
ethyl 3-benzylamino-4-methylpentanoate,
n-octyl 3-benzylamino-4-methylpentanoate,
2-chloroethyl 3-benzylamino-4-methylpentanoate,
2,2,2-trichloroethyl 3-benzylamino-4-methylpentanoate,
2,2,2-trifluoroethyl 3-benzylamino-4-methylpentanoate,
methyl 3-(2-methylbenzyl)-4-methylpentanoate,
methyl 3-(4-methylbenzyl)-4-methylpentanoate,
methyl 3-(2-methoxybenzyl)-4-methylpentanoate,
methyl 3-(4-methoxybenzyl)amino-4-methylpentanoate,
butyl 3-(2-chlorobenzyl)amino-4-methylpentanoate,
methyl 3-(4-chlorobenzyl)amino-4-methylpentanoate,
methyl 3-(4-nitrobenzyl)amino-4-methylpentanoate,
methyl 3-(2-methoxybenzyl)amino-4-methylpentanoate,
methyl 3-(4-methoxybenzyl)amino-4-methylpentanoate,
methyl 3-(3,4-dimethoxybenzyl)amino-4-methylpentanoate,
methyl 3-(3,4-methylenedioxybenzyl)amino-4-methylpentanoate,
methyl 3-benzylamino-4-chlorobutyrate,
ethyl 3-benzylamino-4-chlorobutyrate,
methyl 3-benzylamino-4-hydroxybutyrate,
methyl 3-benzylamino-3-phenylpropionate,
ethyl 3-benzylamino-3-phenylpropionate,
2-chloroethyl 3-benzylamino-3-phenylpropionate,
2,2,2-trichloroethyl 3-benzylamino-3-phenylpropionate,
2,2,2-trifluoroethyl 3-benzylamino-3-phenylpropionate,
2-cyanoethyl 3-benzylamino-3-phenylpropionate,
methyl 3-(4-methoxybenzylamino)-3-phenylpropionate,
methyl 3-(4-hydroxybenzyl)amino-3-phenylpropionate,
methyl 3-(3,4-dimethoxybenzyl)amino-3-phenylpropionate,
methyl 3-(3,4-methylenedioxybenzyl)amino-3-phenylpropionate,
methyl 3-(1-phenylethyl)amino-3-phenylpropionate,
methyl 3-(1-(1-naphthyl)ethyl)amino-3-phenylpropionate,
methyl 3-diphenylmethylamino-3-phenylpropionate,
methyl 3-tritylamino-3-phenylpropionate,
methyl 3-benzylamino-3-(2-fluorophenyl)propionate,
methyl 3-benzylamino-3-(4-fluorophenyl)propionate,
ethyl 3-benzylamino-3-(4-fluorophenyl)propionate,
methyl 3-diphenylmethylamino-3-(4-fluorophenyl)propionate,
methyl 3-benzylamino-3-(2-chlorophenyl)phenylpropionate,
methyl 3-benzylamino-3-(4-chlorophenyl)phenylpropionate,
methyl 3-benzylamino-3-(4-hydroxyphenyl)propionate,
ethyl 3-benzylamino-3-(2-hydroxyphenyl)propionate,
methyl 3-benzylamino-3-(2-methoxyphenyl)propionate,
methyl 3-benzylamino-3-(4-methoxyphenyl)propionate,
ethyl 3-benzylamino-3-(4-methoxyphenyl)propionate,
methyl 3-diphenylmethylamino-3-(4-methoxyphenyl)propionate,
methyl 3-benzylamino-3-(3,4-dimethoxyphenyl)propionate,
ethyl 3-benzylamino-3-(3,4-dimethoxyphenyl)propionate,
methyl 3-diphenylmethylamino-3-(3,4-dimethoxyphenyl)propionate,
methyl 3-benzylamino-3-(3,4-methylenedioxyphenyl)propionate,
ethyl 3-benzylamino-3-(3,4-methylenedioxyphenyl)propionate,
ethyl 3-diphenylmethylamino-3-(3,4-methylenedioxyphenyl)propionate,
methyl 3-benzylamino-3-(4-tolyl)propionate,
ethyl 3-benzylamino-3-(4-tolyl)propionate,
methyl 3-diphenylmethylamino-3-(4-tolyl)propionate,
methyl 3-benzylamino-3-(2-tolyl)propionate,
methyl 3-benzylamino-4-phenylbutyrate,
methyl 3-benzylamino-4-(4-fluorophenyl)butyrate,
methyl 3-benzylamino-4-(2-fluorophenyl)butyrate,
methyl 3-benzylamino-4-(4-chlorophenyl)butyrate,
methyl 3-benzylamino-4-(4-methoxyphenyl)butyrate,
methyl 3-benzylamino-4-(2-methoxyphenyl)butyrate,
methyl 3-benzylamino-4-(3,4-dimethoxyphenyl)butyrate,
methyl 3-benzylamino-4-(4-hydroxyphenyl)butyrate, methyl 3-benzylamino-5-phenylpentanoate,
methyl 3-benzylamino-5-(4-fluorophenyl)pentanoate,
methyl 3-benzylamino-5-(4-chlorophenyl)pentanoate,
methyl 3-benzylamino-5-(2-fluorophenyl)pentanoate,
methyl 3-benzylamino-5-(4-methoxyphenyl)pentanoate,
methyl 3-benzylamino-5-(2-methoxyphenyl)pentanoate,
methyl 3-benzylamino-5-(3,4-dimethoxyphenyl)pentanoate,
methyl 3-benzhydrylamino-5-phenylpentanoate,
methyl 3-(1-phenylethyl)amino-4-chlorobutyrate,
ethyl 3-benzhydrylamino-4-hydroxybutyrate,
methyl 3-benzhydrylaminopentanoate,
methyl 3-(1-phenylethyl)amino-4-methylpentanoate,
ethyl 3-benzhydrylamino-4-methylpentanoate, more preferably
methyl 3-benzylaminobutyrate,
ethyl 3-benzylaminobutyrate,
methyl 3-benzylamino-3-phenylpropionate
ethyl 3-benzylamino-3-phenylpropionate
methyl 3-benzylamino-3-(4-tolyl)propionate,
ethyl 3-benzylamino-3-(4-tolyl)propionate,
methyl 3-benzylamino-3-(4-fluorophenyl)propionate
methyl 3-benzylamino-3-(3,4-methylenedioxyphenyl)propionate,
ethyl 3-benzylamino-3-(3,4-methylenedioxyphenyl)propionate,
methyl 3-benzylaminopentanoate,
ethyl 3-benzylaminopentanoate,
methyl 3-benzylaminohexanoate,
ethyl 3-benzylaminohexanoate,
methyl 3-benzylamino-4-methylpentanoate, and
ethyl 3-benzylamino-4-methylpentanoate.

Also, specific examples of Compound (I-b) having the above-mentioned Ar, $R^3$, $R^4$ and $R^5$ may include, for example,
methyl 1-benzyl-2-homopipecolate,
ethyl 1-benzyl-2-homopipecolate,
n-butyl 1-benzyl-2-homopipecolate,
n-octyl 1-benzyl-2-homopipecolate,
2-chloroethyl 1-benzyl-2-homopipecolate,
2,2,2-trichloroethyl 1-benzyl-2-homopipecolate,
2,2,2-trifluoroethyl 1-benzyl-2-homopipecolate,
2-cyanoethyl 1-benzyl-2-homopipecolate,
methyl 1-(4-methylbenzyl)-2-homopipecolate,
ethyl 1-(hydroxybenzyl)-2-homopipecolate,
methyl 1-(3,4-dihydroxybenzyl)-2-homopipecolate,
methyl 1-(4-chlorobenzyl)-2-homopipecolate,
ethyl 1-(4-fluorobenzyl)-2-homopipecolate,
methyl 1-(4-methoxybenzyl)-2-homopipecolate,
methyl 1-(3,4-dimethoxybenzyl)-2-homopipecolate,
methyl 1-(3,4-methylenedioxybenzyl)-2-homopipecolate,
methyl 1-(4-nitrobenzyl)-2-homopipecolate,
methyl 1-(1-naphthylmethyl)-2-homopipecolate,
methyl 1-(2-naphthylmethyl)-2-homopipecolate,
methyl 1-(1-phenylethyl)-2-homopipecolate,
methyl 1-(1-(2-chlorophenyl)ethyl)-2-homopipecolate,
methyl 1-(1-(1-naphthyl)ethyl)-2-homopipecolate,
methyl 1-diphenylmethyl-2-homopipecolate,
2,2,2-trifluoroethyl 1-trityl-2-homopipecolate,
methyl 1-di(4-methoxyphenyl)methyl-2-homopipecolate, etc., preferably
methyl 1-benzyl-2-homopipecolate,
ethyl 1-benzyl-2-homopipecolate,
n-octyl 1-benzyl-2-homopipecolate,
2-chloroethyl 1-benzyl-2-homopipecolate,
2,2,2-trichloroethyl 1-benzyl-2-homopipecolate,
2,2,2-trifluoroethyl 1-benzyl-2-homopipecolate,
methyl 1-(4-methylbenzyl)-2-homopipecolate,
ethyl 1-(hydroxybenzyl)-2-homopipecolate,
methyl 1-(4-chlorobenzyl)-2-homopipecolate,
methyl 1-(4-methoxybenzyl)-2-homopipecolate,
methyl 1-(4-nitrobenzyl)-2-homopipecolate,
methyl 1-(1-naphthylmethyl)-2-homopipecolate,
methyl 1-(1-phenylethyl)-2-homopipecolate,
methyl 1-(1-(1-naphthyl)ethyl)-2-homopipecolate,
methyl 1-diphenylmethyl-2-homopipecolate, more preferably
methyl 1-benzyl-2-homopipecolate,
ethyl 1-benzyl-2-homopipecolate,
methyl 1-(4-methoxybenzyl)-2-homopipecolate,
methyl 1-(1-phenylethyl)-2-homopipecolate,
methyl 1-diphenylmethyl-2-homopipecolate.

As the hydrolase to be used in the hydrolysis of the present invention, there may be mentioned, for example, protease, esterase, lipase and the like, preferably a lipase of microorganisms which are capable of isolating from yeast or bacteria, more preferably a lipase originated from *Pseudomonas* (for example, AMANO PS (available from Amanoenzyme Co.), etc.), a lipase originated from *Candida antarctica* (for example, CHIRAZYME L-2 (available from Roche AG), etc.), particularly preferably a lipase originated from *Candida antarctica* is used. Incidentally, these hydrolases may be used in a natural form or a commercially available product as such as a fixed enzyme, and may be used alone or in combination of two or more kinds.

An amount of the above-mentioned hydrolase to be used is preferably 0.1 to 1000 mg, more preferably 1 to 200 mg based on 1 g of Compound (I).

The hydrolysis reaction of the present invention is preferably carried out in an aqueous solution, in a buffer solvent, in a 2-phase solvent of an organic solvent and water, or in a 2-phase solvent of an organic solvent and a buffer.

As the above-mentioned water, purified water such as deionized water, distilled water, etc., is preferably used. Incidentally, when water is used as the solvent, a weak base such as potassium hydrogen carbonate or sodium hydrogen carbonate may be present in the reaction system to neutralize the formed Compound (II). An amount of the above-mentioned weak base to be used is preferably 0.5 to 1.0 mol based on 1 mol of Compound (II).

As the above-mentioned buffer solution, there may be mentioned, for example, an aqueous solution of an inorganic acid salt such as an aqueous sodium phosphate solution, an aqueous potassium phosphate solution, etc.; an aqueous solution of an organic acid salt such as an aqueous sodium acetate solution, an aqueous sodium citrate solution, etc., preferably an aqueous solution of an inorganic acid salt, more preferably aqueous sodium phosphate solution is used. These aqueous solutions may be used alone or in admixture of two kinds or more.

A concentration of the buffer solution is preferably 0.01 to 2 mol/l, more preferably 0.05 to 0.5 mol/l, and a pH of the buffer solution is preferably 4 to 9, more preferably 6 to 8.

As the above-mentioned organic solvent, there may be mentioned, for example, an aliphatic hydrocarbon such as n-pentane, n-hexane, n-heptane, n-octane, cyclopentane, cyclohexane, cyclopentane, etc.; an aromatic hydrocarbon such as benzene, toluene, xylene, etc.; an ether such as diethyl ether, t-butyl methyl ether, diisopropyl ether, tetrahydrofuran, 1,4-dioxane, etc., preferably n-hexane, n-heptane, cyclopentane, cyclohexane, toluene, diisopropyl ether, t-butyl methyl ether, tetrahydrofuran, more preferably n-hexane, cyclohexane, diisopropyl ether, t-butyl methyl ether and/or tetrahydrofuran is/are used.

An amount of the solvent to be used (water solvent, a buffer solution solvent, a 2-phase solvent of an organic solvent and water, or a 2-phase solvent of an organic solvent and a buffer solution) in the hydrolysis reaction of the present invention is preferably 2 to 200 ml, more preferably 5 to 80 ml based on 1 g of Compound (I).

In the hydrolysis reaction of the present invention, an amount of the organic solvent to be used when the 2-phase solvent of an organic solvent and water or the 2-phase solvent of an organic solvent and a buffer solution is used is preferably 0.1 to 10 ml, more preferably 0.5 to 5 ml based on 1 ml of water or the buffer solution.

The hydrolysis reaction of the present invention can be carried out, for example, by mixing Compound (I), a hydrolase and a solvent (water solvent, a buffer solvent, a 2-phase solvent of an organic solvent and water, or a 2-phase solvent of an organic solvent and a buffer solution), and reacting the mixture under stirring, and the like. The reaction temperature at that time is preferably 0 to 80° C., more preferably 10 to 50° C., and the reaction pressure is not specifically limited.

Compound (II) and Compound (III) obtained by the hydrolysis reaction of the present invention can be obtained by, for example, after completion of the reaction, removing insoluble materials by filtrating the reaction mixture, extracting the obtained filtrate with an organic solvent, and concentrating the extract to obtain the product as a mixture of Compound (II) and Compound (III). Incidentally, they can be isolated respectively from the above-mentioned mixture by a general purifying method such as crystallization, recrystallization, distillation, column chromatography, etc., by preferably column chromatography, more preferably isolated by silica gel column chromatography.

Specific examples of Compound (II-a) obtained by the hydrolysis reaction of the present invention may include, for example,
optically active (R or S)-3-benzylaminobutyric acid,
optically active (R or S)-3-(4-chlorobenzylamino)butyric acid,
optically active (R or S)-3-(4-fluorobenzylamino)butyric acid,
optically active (R or S)-3-(4-methoxybenzylamino)acetic acid,
optically active (R or S)-3-(4-hydroxybenzyl)aminoacetic acid,
optically active (R or S)-3-(4-methylbenzyl)aminobutyric acid,
optically active (R or S)-3-(3,4-dimethoxybenzyl)aminobutyric acid,
optically active (R or S)-3-(3,4-methylenedioxybenzyl)aminobutyric acid,
optically active (R or S)-3-(4-nitrobenzyl)aminobutyric acid,
optically active (R or S)-3-(1-naphthylmethyl)aminobutyric acid,
optically active (R or S)-3-(1-phenylethyl)aminobutyric acid,
optically active (R or S)-3-(1-(2-chlorophenyl)ethyl)aminobutyric acid,
optically active (R or S)-3-(1-(1-naphthyl)ethyl)aminobutyric acid,
optically active (R or S)-3-diphenylmethylaminobutyric acid,
optically active (R or S)-3-tritylaminobutyric acid,
optically active (R or S)-3-benzylaminopentanoic acid,
optically active (R or S)-3-(4-chlorobenzylamino)pentanoic acid,
optically active (R or S)-3-(4-methoxybenzyl)aminopentanoic acid,
optically active (R or S)-3-(4-nitrobenzyl)aminopentanoic acid,
optically active (R or S)-3-benzylaminohexanoic acid,
optically active methyl (R or S)-3-benzylamino-4-methylpentanoate,
optically active (R or S)-3-(2-methylbenzyl)-4-methylpentanoic acid,
optically active (R or S)-3-(3-methylbenzyl)-4-methylpentanoic acid,
optically active (R or S)-3-(4-methylbenzyl)-4-methylpentanoic acid,
optically active (R or S)-3-(2-methoxybenzyl)amino-4-methylpentanoic acid,
optically active (R or S)-3-(3-methoxybenzyl)amino-4-methylpentanoic acid,
optically active (R or S)-3-(4-methoxybenzyl)amino-4-methylpentanoic acid,
optically active (R or S)-3-(2-chlorobenzyl)amino-4-methylpentanoic acid,
optically active (R or S)-3-(3-chlorobenzyl)amino-4-methylpentanoic acid,
optically active (R or S)-3-(4-chlorobenzyl)amino-4-methylpentanoic acid,
optically active (R or S)-3-(2-bromobenzyl)amino-4-methylpentanoic acid,
optically active (R or S)-3-(3-bromobenzyl)amino-4-methylpentanoic acid,
optically active (R or S)-3-(4-bromobenzyl)amino-4-methylpentanoic acid,
optically active (R or S)-3-(2-fluorobenzyl)amino-4-methylpentanoic acid,
optically active (R or S)-3-(2-nitrobenzyl)amino-4-methylpentanoic acid,
optically active (R or S)-3-(4-nitrobenzyl)amino-4-methylpentanoic acid,
optically active (R or S)-3-(2-methoxybenzyl)amino-4-methylpentanoic acid,
optically active (R or S)-3-(3,4-dimethoxybenzyl)amino-4-methylpentanoic acid,
optically active (R or S)-3-(3,4-methylenedioxybenzyl)amino-4-methylpentanoic acid,
optically active (R or S)-3-benzylamino-4-chlorobutyric acid,
optically active (R or S)-3-benzylamino-4-hydroxybutyric acid,
optically active (R or S)-3-benzylamino-3-phenylpropionic acid
optically active (R or S)-3-(4-methoxybenzylamino)-3-phenylpropionic acid,
optically active (R or S)-3-(4-hydroxybenzyl)amino-3-phenylpropionic acid,
optically active (R or S)-3-(4-methylbenzyl)amino-3-phenylpropionic acid,
optically active (R or S)-3-(3,4-dimethoxybenzyl)amino-3-phenylpropionic acid,
optically active (R or S)-3-(3,4-methylenedioxybenzyl)amino-3-phenylpropionic acid,
optically active (R or S)-3-(4-nitrobenzyl)amino-3-phenylpropionic acid,
optically active (R or S)-3-(1-phenylethyl)amino-3-phenylpropionic acid,
optically active (R or S)-3-(1-(1-naphthyl)ethyl)amino-3-phenylpropionic acid,
optically active (R or S)-3-diphenylmethylamino-3-phenylpropionic acid, optically active (R or S)-3-tritylamino-3-phenylpropionic acid,
optically active (R or S)-3-benzylamino-3-(2-fluorophenyl)propionic acid,
optically active (R or S)-3-benzylamino-3-(4-fluorophenyl)propionic acid,
optically active (R or S)-3-diphenylmethylamino-3-(4-fluorophenyl)propionic acid,
optically active (R or S)-3-benzylamino-3-(2-chlorophenyl)phenylpropionic acid,
optically active (R or S)-3-benzylamino-3-(4-chlorophenyl)phenylpropionic acid,
optically active (R or S)-3-benzylamino-3-(4-bromophenyl)propionic acid,
optically active (R or S)-3-benzylamino-3-(4-iodophenyl)propionic acid,
optically active methyl (R or S)-3-benzylamino-3-(4-hydroxyphenyl)propionate,
optically active (R or S)-3-benzylamino-3-(2-hydroxyphenyl)propionic acid,
optically active (R or S)-3-benzylamino-3-(2-methoxyphenyl)propionic acid,
optically active (R or S)-3-benzylamino-3-(4-methoxyphenyl)propionic acid,
optically active (R or S)-3-diphenylmethylamino-3-(4-methoxyphenyl)propionic acid,
optically active (R or S)-3-benzylamino-3-(3,4-dimethoxyphenyl)propionic acid,
optically active (R or S)-3-diphenylmethylamino-3-(3,4-dimethoxyphenyl)propionic acid,
optically active (R or S)-3-benzylamino-3-(3,4-methylenedioxyphenyl)propionic acid,
3-diphenylmethylamino-3-(3,4-methylenedioxyphenyl)propionic acid,
optically active (R or S)-3-benzylamino-3-(4-tolyl)propionic acid,
optically active (R or S)-3-diphenylmethylamino-3-(4-tolyl)propionic acid,
optically active (R or S)-3-benzylamino-3-(2-tolyl)propionic acid,
optically active (R or S)-3-benzylamino-4-phenylbutyric acid,
optically active (R or S)-3-benzylamino-4-(4-fluorophenyl)butyric acid,
optically active (R or S)-3-benzylamino-4-(2-fluorophenyl)butyric acid,
optically active (R or S)-3-benzylamino-4-(4-chlorophenyl)butyric acid,
optically active (R or S)-3-benzylamino-4-(4-iodophenyl)butyric acid,
optically active (R or S)-3-benzylamino-4-(4-methoxyphenyl)butyric acid,
optically active (R or S)-3-benzylamino-4-(2-methoxyphenyl)butyric acid,
optically active (R or S)-3-benzylamino-4-(3,4-dimethoxyphenyl)butyric acid,
optically active (R or S)-3-benzylamino-4-(4-hydroxyphenyl)butyric acid,
optically active (R or S)-3-benzylamino-5-phenylpentanoic acid,
optically active (R or S)-3-benzylamino-5-(4-fluorophenyl)pentanoic acid,
optically active (R or S)-3-benzylamino-5-(4-chlorophenyl)pentanoic acid,
optically active (R or S)-3-benzylamino-5-(2-fluorophenyl)pentanoic acid,
optically active (R or S)-3-benzylamino-5-(4-methoxyphenyl)pentanoic acid,
optically active (R or S)-3-benzylamino-5-(2-methoxyphenyl)pentanoic acid,
optically active (R or S)-3-benzylamino-5-(3,4-dimethoxyphenyl)pentanoic acid,
optically active (R or S)-3-(1-phenylethyl)amino-5-phenylpentanoic acid,
optically active (R or S)-3-benzhydrylamino-5-phenylpentanoic acid,
optically active (R or S)-3-(1-phenylethyl)amino-4-chlorobutyric acid,
optically active (R or S)-3-benzhydrylamino-4-hydroxybutyric acid,
optically active (R or S)-3-(1-phenylethyl)amino-4-hydroxybutyric acid,
optically active (R or S)-3-benzhydrylamino-4-hydroxybutyric acid,
optically active (R or S)-3-benzhydrylaminopentanoic acid,
optically active (R or S)-3-(1-phenylethyl)amino-4-methylpentanoic acid,
optically active (R or S)-3-benzhydrylamino-4-methylpentanoic acid,
optically active (R or S)-3-(1-naphthylmethyl)aminobutyric acid,
optically active (R or S)-3-(2-naphthylmethyl)aminobutyric acid,
optically active (R or S)-3-(2-naphthylmethyl)aminopentanoic acid,
optically active (R or S)-3-(2-naphthylmethyl)amino-4-methylpentanoic acid,
optically active (R or S)-3-(1-(1-naphthyl)ethyl)amino-4-methylpentanoic acid, and the like, preferably
optically active (R or S)-3-benzylaminobutyric acid,
optically active (R or S)-3-(4-chlorobenzylamino)butyric acid,
optically active (R or S)-3-(4-fluorobenzylamino)butyric acid,
optically active (R or S)-3-(4-methoxybenzylamino)acetic acid,
optically active (R or S)-3-(4-hydroxybenzyl)aminoacetic acid,
optically active (R or S)-3-(4-methylbenzyl)aminobutyric acid,
optically active (R or S)-3-(3,4-dimethoxybenzyl)aminobutyric acid,
optically active (R or S)-3-(3,4-methylenedioxybenzyl)aminobutyric acid,
optically active (R or S)-3-(4-nitrobenzyl)aminobutyric acid,
optically active (R or S)-3-(1-naphthylmethyl)aminobutyric acid,
optically active (R or S)-3-(1-phenylethyl)aminobutyric acid,
optically active (R or S)-3-(1-(1-naphthyl)ethyl)aminobutyric acid,
optically active (R or S)-3-diphenylmethylaminobutyric acid,
optically active (R or S)-3-benzylaminopentanoic acid,
optically active (R or S)-3-(4-chlorobenzylamino)pentanoic acid
optically active (R or S)-3-(4-methoxybenzylamino)pentanoic acid,
optically active (R or S)-3-(4-nitrobenzylamino)pentanoic acid,
optically active (R or S)-3-benzylaminohexanoic acid,
optically active (R or S)-3-benzylamino-4-methylpentanoic acid, optically active (R or S)-3-(2-methylbenzyl)-4-methylpentanoic acid,
optically active (R or S)-3-(4-methylbenzyl)-4-methylpentanoic acid,
optically active (R or S)-3-(2-methoxybenzyl)-4-methylpentanoic acid,
optically active (R or S)-3-(4-methoxybenzyl)amino-4-methylpentanoic acid,
optically active (R or S)-3-(2-chlorobenzyl)amino-4-methylpentanoic acid,
optically active (R or S)-3-(4-chlorobenzyl)amino-4-methylpentanoic acid,
optically active (R or S)-3-(4-nitrobenzyl)amino-4-methylpentanoic acid,
optically active (R or S)-3-(2-methoxybenzyl)amino-4-methylpentanoic acid,
optically active (R or S)-3-(4-methoxybenzyl)amino-4-methylpentanoic acid,
optically active (R or S)-3-(3,4-dimethoxybenzyl)amino-4-methylpentanoic acid,
optically active (R or S)-3-(3,4-methylenedioxybenzyl)amino-4-methylpentanoic acid,
optically active (R or S)-3-benzylamino-4-chlorobutyric acid,
optically active (R or S)-3-benzylamino-4-hydroxybutyric acid,
optically active (R or S)-3-benzylamino-3-phenylpropionic acid,
optically active (R or S)-3-(4-methoxybenzylamino)-3-phenylpropionic acid,
optically active (R or S)-3-(4-hydroxybenzyl)amino-3-phenylpropionic acid,
optically active (R or S)-3-(3,4-dimethoxybenzyl)amino-3-phenylpropionic acid,
optically active (R or S)-3-(3,4-methylenedioxybenzyl)amino-3-phenylpropionic acid,
optically active (R or S)-3-(1-phenylethyl)amino-3-phenylpropionic acid,
optically active (R or S)-3-(1-(1-naphthyl)ethyl)amino-3-phenylpropionic acid,
optically active (R or S)-3-diphenylmethylamino-3-phenylpropionic acid,
optically active (R or S)-3-tritylamino-3-phenylpropionic acid,
optically active (R or S)-3-benzylamino-3-(2-fluorophenyl)propionic acid,
optically active (R or S)-3-benzylamino-3-(4-fluorophenyl)propionic acid,
optically active (R or S)-3-diphenylmethylamino-3-(4-fluorophenyl)propionic acid,
optically active (R or S)-3-benzylamino-3-(2-chlorophenyl)phenylpropionic acid,
optically active (R or S)-3-benzylamino-3-(4-chlorophenyl)phenylpropionic acid,
optically active (R or S)-3-benzylamino-3-(4-hydroxyphenyl)propionic acid,
optically active (R or S)-3-benzylamino-3-(2-hydroxyphenyl)propionic acid,
optically active (R or S)-3-benzylamino-3-(2-methoxyphenyl)propionic acid,
optically active (R or S)-3-benzylamino-3-(4-methoxyphenyl)propionic acid,
optically active (R or S)-3-diphenylmethylamino-3-(4-methoxyphenyl)propionic acid,
optically active (R or S)-3-benzylamino-3-(3,4-dimethoxyphenyl)propionic acid,
optically active (R or S)-3-diphenylmethylamino-3-(3,4-dimethoxyphenyl)propionic acid,
optically active (R or S)-3-benzylamino-3-(3,4-methylenedioxyphenyl)propionic acid,
optically active (R or S)-3-diphenylmethylamino-3-(3,4-methylenedioxyphenyl)propionic acid,
optically active (R or S)-3-benzylamino-3-(4-tolyl)propionic acid,
optically active (R or S)-3-diphenylmethylamino-3-(4-tolyl)propionic acid,
optically active (R or S)-3-benzylamino-3-(2-tolyl)propionic acid,
optically active (R or S)-3-benzylamino-4-phenylbutyric acid,
optically active (R or S)-3-benzylamino-4-(4-fluorophenyl)butyric acid,
optically active (R or S)-3-benzylamino-4-(2-fluorophenyl)butyric acid,
optically active (R or S)-3-benzylamino-4-(4-chlorophenyl)butyric acid,
optically active (R or S)-3-benzylamino-4-(4-methoxyphenyl)butyric acid,
optically active (R or S)-3-benzylamino-4-(2-methoxyphenyl)butyric acid,
optically active (R or S)-3-benzylamino-4-(3,4-dimethoxyphenyl)butyric acid,
optically active (R or S)-3-benzylamino-4-(4-hydroxyphenyl)butyric acid,
optically active (R or S)-3-benzylamino-5-phenylpentanoic acid,
optically active (R or S)-3-benzylamino-5-(4-fluorophenyl)pentanoic acid,
optically active (R or S)-3-benzylamino-5-(4-chlorophenyl)pentanoic acid,
optically active (R or S)-3-benzylamino-5-(2-fluorophenyl)pentanoic acid,
optically active (R or S)-3-benzylamino-5-(4-methoxyphenyl)pentanoic acid,
optically active (R or S)-3-benzylamino-5-(2-methoxyphenyl)pentanoic acid,
optically active (R or S)-3-benzylamino-5-(3,4-dimethoxyphenyl)pentanoic acid,
optically active (R or S)-3-benzhydrylamino-5-phenylpentanoic acid,
optically active (R or S)-3-(1-phenylethyl)amino-4-chlorobutyric acid,
optically active (R or S)-3-benzhydrylamino-4-hydroxybutyric acid,
optically active (R or S)-3-benzhydrylaminopentanoic acid,
optically active (R or S)-3-(1-phenylethyl)amino-4-methylpentanoic acid,
optically active (R or S)-3-benzhydrylamino-4-methylpentanoic acid, more preferably
optically active (R or S)-3-benzylaminobutyric acid,
optically active (R or S)-3-benzylamino-3-phenylpropionic acid,
optically active (R or S)-3-benzylamino-3-(4-tolyl)propionic acid,
optically active (R or S)-3-benzylamino-3-(4-fluorophenyl)propionic acid,
optically active (R or S)-3-benzylamino-3-(3,4-methylenedioxyphenyl)propionic acid,
optically active (R or S)-3-benzylamino-3-(3,4-methylenedioxyphenyl)propionic acid,
optically active (R or S)-3-benzylaminopentanoic acid, optically active (R or S)-3-benzylaminohexanoic acid, and
optically active (R or S)-3-benzylamino-4-methylpentanoic acid.

Specific examples of unreacted Compound (III-a) (having reverse steric absolute configuration to that of Compound (II-a)) which was not reacted in the hydrolysis reaction of the present invention may include, for example,
optically active methyl (S or R)-3-benzylaminobutyrate,
optically active ethyl (S or R)-3-benzylaminobutyrate,
optically active n-propyl (S or R)-3-benzylaminobutyrate,
optically active n-butyl (S or R)-3-benzylaminobutyrate,
optically active n-octyl (S or R)-3-benzylaminobutyrate,
optically active 2-chloroethyl (S or R)-3-benzylaminobutyrate,
optically active 2,2,2-trichloroethyl (S or R)-3-benzylaminobutyrate,
optically active 2,2,2-trifluoroethyl (S or R)-3-benzylaminobutyrate,
optically active 2-cyanoethyl (S or R)-3-benzylaminobutyrate,
optically active methyl (S or R)-3-(4-chlorobenzylamino)butyrate,
optically active methyl (S or R)-3-(4-fluorobenzylamino)butyrate,
optically active methyl (S or R)-3-(4-methoxybenzylamino)acetate,
optically active methyl (S or R)-3-(4-hydroxybenzyl)aminoacetate,
optically active methyl (S or R)-3-(4-methylbenzyl)aminobutyrate,
optically active methyl (S or R)-3-(3,4-dimethoxybenzyl)aminobutyrate,
optically active methyl (S or R)-3-(3,4-methylenedioxybenzyl)aminobutyrate,
optically active methyl (S or R)-3-(4-nitrobenzyl)aminobutyrate,
optically active methyl (S or R)-3-(1-naphthylmethyl)aminobutyrate,
optically active methyl (S or R)-3-(1-phenylethyl)aminobutyrate,
optically active methyl (S or R)-3-(1-(2-chlorophenyl)ethyl)aminobutyrate,
optically active methyl (S or R)-3-(1-(1-naphthyl)ethyl)aminobutyrate,
optically active methyl (S or R)-3-diphenylmethylaminobutyrate,
optically active methyl (S or R)-3-tritylaminobutyrate,
optically active methyl (S or R)-3-benzylaminopentanoate,
optically active ethyl (S or R)-3-benzylaminopentanoate,
optically active 2,2,2-trifluoroethyl (S or R)-3-benzylaminopentanoate,
optically active methyl (S or R)-3-(4-chlorobenzylamino)pentanoate,
optically active methyl (S or R)-3-(4-methoxybenzylamino)pentanoate,
optically active ethyl (S or R)-3-(4-nitrobenzylamino)pentanoate,
optically active methyl (S or R)-3-benzylaminohexanoate,
optically active ethyl (S or R)-3-benzylaminohexanoate,
optically active 2,2,2-trichloroethyl (S or R)-3-benzylaminohexanoate,
optically active 2,2,2-trifluoroethyl (S or R)-3-benzylaminohexanoate,
optically active methyl (S or R)-3-benzylamino-4-methylpentanoate,
optically active ethyl (S or R)-3-benzylamino-4-methylpentanoate,
optically active n-propyl (S or R)-3-benzylamino-4-methylpentanoate,
optically active n-butyl (S or R)-3-benzylamino-4-methylpentanoate,
optically active n-pentyl (S or R)-3-benzylamino-4-methylpentanoate,
optically active n-octyl (S or R)-3-benzylamino-4-methylpentanoate,
optically active 2-chloroethyl (S or R)-3-benzylamino-4-methylpentanoate,
optically active 2,2,2-trichloroethyl (S or R)-3-benzylamino-4-methylpentanoate,
optically active 2,2,2-trifluoroethyl (S or R)-3-benzylamino-4-methylpentanoate,
optically active methyl (S or R)-3-(2-methylbenzyl)-4-methylpentanoate,
optically active methyl (S or R)-3-(3-methylbenzyl)-4-methylpentanoate,
optically active methyl (S or R)-3-(4-methylbenzyl)-4-methylpentanoate,
optically active methyl (S or R)-3-(2-methoxybenzyl)-4-methylpentanoate,
optically active methyl (S or R)-3-(3-methoxybenzyl)amino-4-methylpentanoate,
optically active methyl (S or R)-3-(4-methoxybenzyl)amino-4-methylpentanoate,
optically active butyl (S or R)-3-(2-chlorobenzyl)amino-4-methylpentanoate,
optically active ethyl (S or R)-3-(3-chlorobenzyl)amino-4-methylpentanoate,
optically active methyl (S or R)-3-(4-chlorobenzyl)amino-4-methylpentanoate,
optically active methyl (S or R)-3-(2-bromobenzyl)amino-4-methylpentanoate,
optically active methyl (S or R)-3-(3-bromobenzyl)amino-4-methylpentanoate,
optically active ethyl (S or R)-3-(4-bromobenzyl)amino-4-methylpentanoate,
optically active methyl (S or R)-3-(2-fluorobenzyl)amino-4-methylpentanoate,
optically active methyl (S or R)-3-(2-nitrobenzyl)amino-4-methylpentanoate,
optically active methyl (S or R)-3-(4-nitrobenzyl)amino-4-methylpentanoate,
optically active methyl (S or R)-3-(2-methoxybenzyl)amino-4-methylpentanoate,
optically active methyl (S or R)-3-(3-methoxybenzyl)amino-4-methylpentanoate,
optically active methyl (S or R)-3-(4-methoxybenzyl)amino-4-methylpentanoate,
optically active methyl (S or R)-3-(3,4-dimethoxybenzyl)amino-4-methylpentanoate,
optically active methyl (S or R)-3-(3,4-methylenedioxybenzyl)amino-4-methylpentanoate,
optically active methyl (S or R)-3-benzylamino-4-chlorobutyrate,
optically active ethyl (S or R)-3-benzylamino-4-chlorobutyrate,
optically active methyl (S or R)-3-benzylamino-4-hydroxybutyrate,
optically active ethyl (S or R)-3-benzylamino-4-hydroxybutyrate,
optically active methyl (S or R)-3-benzylamino-3-phenylpropionate,
optically active ethyl (S or R)-3-benzylamino-3-phenylpropionate, optically active n-propyl (S or R)-3-benzylamino-3-phenylpropionate,
optically active n-butyl (S or R)-3-benzylamino-3-phenylpropionate,
optically active n-octyl (S or R)-3-benzylamino-3-phenylpropionate,
optically active 2-chloroethyl (S or R)-3-benzylamino-3-phenylpropionate,
optically active 2,2,2-trichloroethyl (S or R)-3-benzylamino-3-phenylpropionate,
optically active 2,2,2-trifluoroethyl (S or R)-3-benzylamino-3-phenylpropionate,
optically active 2-cyanoethyl (S or R)-3-benzylamino-3-phenylpropionate,
optically active methyl (S or R)-3-(4-methoxybenzylamino)-3-phenylpropionate,
optically active methyl (S or R)-3-(4-hydroxybenzyl)amino-3-phenylpropionate,
optically active methyl (S or R)-3-(4-methylbenzyl)amino-3-phenylpropionate,
optically active methyl (S or R)-3-(3,4-dimethoxybenzyl)amino-3-phenylpropionate,
optically active methyl (S or R)-3-(3,4-methylenedioxybenzyl)amino-3-phenylpropionate,
optically active methyl (S or R)-3-(4-nitrobenzyl)amino-3-phenylpropionate,
optically active methyl (S or R)-3-(1-phenylethyl)amino-3-phenylpropionate,
optically active methyl (S or R)-3-(1-(1-naphthyl)ethyl)amino-3-phenylpropionate,
optically active methyl (S or R)-3-diphenylmethylamino-3-phenylpropionate,
optically active methyl (S or R)-3-tritylamino-3-phenylpropionate,
optically active methyl (S or R)-3-benzylamino-3-(2-fluorophenyl)propionate,
optically active methyl (S or R)-3-benzylamino-3-(4-fluorophenyl)propionate,
optically active ethyl (S or R)-3-benzylamino-3-(4-fluorophenyl)propionate,
optically active methyl (S or R)-3-diphenylmethylamino-3-(4-fluorophenyl)propionate,
optically active methyl (S or R)-3-benzylamino-3-(2-chlorophenyl)phenylpropionate,
optically active methyl (S or R)-3-benzylamino-3-(4-chlorophenyl)phenylpropionate,
optically active methyl (S or R)-3-benzylamino-3-(4-bromophenyl)propionate,
optically active ethyl (S or R)-3-benzylamino-3-(4-iodophenyl)propionate,
optically active methyl (S or R)-3-benzylamino-3-(4-hydroxyphenyl)propionate,
optically active ethyl (S or R)-3-benzylamino-3-(2-hydroxyphenyl)propionate,
optically active methyl (S or R)-3-benzylamino-3-(2-methoxyphenyl)propionate,
optically active methyl (S or R)-3-benzylamino-3-(4-methoxyphenyl)propionate,
optically active ethyl (S or R)-3-benzylamino-3-(4-methoxyphenyl)propionate,
optically active methyl (S or R)-3-diphenylmethylamino-3-(4-methoxyphenyl)propionate,
optically active methyl (S or R)-3-benzylamino-3-(3,4-dimethoxyphenyl)propionate,
optically active ethyl (S or R)-3-benzylamino-3-(3,4-dimethoxyphenyl)propionate,
optically active methyl (S or R)-3-diphenylmethylamino-3-(3,4-dimethoxyphenyl)propionate,
optically active methyl (S or R)-3-benzylamino-3-(3,4-methylenedioxyphenyl)propionate,
optically active ethyl (S or R)-3-benzylamino-3-(3,4-methylenedioxyphenyl)propionate,
optically active ethyl (S or R)-3-diphenylmethylamino-3-(3,4-methylenedioxyphenyl)propionate,
optically active methyl (S or R)-3-benzylamino-3-(4-tolyl)propionate,
optically active ethyl (S or R)-3-benzylamino-3-(4-tolyl)propionate,
optically active methyl (S or R)-3-diphenylmethylamino-3-(4-tolyl)propionate,
optically active methyl (S or R)-3-benzylamino-3-(2-tolyl)propionate,
optically active methyl (S or R)-3-benzylamino-4-phenylbutyrate,
optically active ethyl (S or R)-3-benzylamino-4-phenylbutyrate,
optically active methyl (S or R)-3-benzylamino-4-(4-fluorophenyl)butyrate,
optically active methyl (S or R)-3-benzylamino-4-(2-fluorophenyl)butyrate,
optically active methyl (S or R)-3-benzylamino-4-(4-chlorophenyl)butyrate,
optically active methyl (S or R)-3-benzylamino-4-(4-iodophenyl)butyrate,
optically active methyl (S or R)-3-benzylamino-4-(4-methoxyphenyl)butyrate,
optically active methyl (S or R)-3-benzylamino-4-(2-methoxyphenyl)butyrate,
optically active methyl (S or R)-3-benzylamino-4-(3,4-dimethoxyphenyl)butyrate,
optically active methyl (S or R)-3-benzylamino-4-(4-hydroxyphenyl)butyrate,
optically active methyl (S or R)-3-benzylamino-5-phenylpentanoate,
optically active methyl (S or R)-3-benzylamino-5-(4-fluorophenyl)pentanoate,
optically active methyl (S or R)-3-benzylamino-5-(4-chlorophenyl)pentanoate,
optically active methyl (S or R)-3-benzylamino-5-(2-fluorophenyl)pentanoate,
optically active methyl (S or R)-3-benzylamino-5-(4-methoxyphenyl)pentanoate,
optically active methyl (S or R)-3-benzylamino-5-(2-methoxyphenyl)pentanoate,
optically active methyl (S or R)-3-benzylamino-5-(3,4-dimethoxyphenyl)pentanoate,
optically active methyl (S or R)-3-(1-phenylethyl)amino-5-phenylpentanoate,
optically active methyl (S or R)-3-benzhydrylamino-5-phenylpentanoate,
optically active methyl (S or R)-3-(1-phenylethyl)amino-4-chlorobutyrate,
optically active ethyl (S or R)-3-benzhydrylamino-4-hydroxybutyrate,
optically active ethyl (S or R)-3-(1-phenylethyl)amino-4-hydroxybutyrate,
optically active ethyl (S or R)-3-benzhydrylamino-4-hydroxybutyrate,
optically active methyl (S or R)-3-(1-phenylethyl)aminobutyrate,
optically active methyl (S or R)-3-benzhydrylaminopentanoate, optically active methyl (S or R)-3-(1-phenylethyl)amino-4-methylpentanoate,
optically active ethyl (S or R)-3-benzhydrylamino-4-methylpentanoate,
optically active methyl (S or R)-3-(1-naphthylmethyl)aminobutyrate,
optically active methyl (S or R)-3-(2-naphthylmethyl)aminobutyrate,
optically active methyl (S or R)-3-(2-naphthylmethyl)aminopentanoate,
optically active methyl (S or R)-3-(2-naphthylmethyl)amino-4-methylpentanoate,
optically active methyl (S or R)-3-(1-(1-naphthyl)ethylamino-4-methylpentanoate, and the like, preferably
optically active methyl (S or R)-3-benzylaminobutyrate,
optically active ethyl (S or R)-3-benzylaminobutyrate,
optically active n-octyl (S or R)-3-benzylaminobutyrate,
optically active 2-chloroethyl (S or R)-3-benzylaminobutyrate,
optically active 2,2,2-trichloroethyl (S or R)-3-benzylaminobutyrate,
optically active 2,2,2-trifluoroethyl (S or R)-3-benzylaminobutyrate,
optically active methyl (S or R)-3-(4-chlorobenzylamino)butyrate,
optically active methyl (S or R)-3-(4-fluorobenzylamino)butyrate,
optically active methyl (S or R)-3-(4-methoxybenzylamino) acetate,
optically active methyl (S or R)-3-(4-hydroxybenzyl)aminoacetate,
optically active methyl (S or R)-3-(4-methylbenzyl)aminobutyrate,
optically active methyl (S or R)-3-(3,4-dimethoxybenzyl) aminobutyrate,
optically active methyl (S or R)-3-(3,4-methylenedioxybenzyl)aminobutyrate,
optically active methyl (S or R)-3-(4-nitrobenzyl)aminobutyrate,
optically active methyl (S or R)-3-(1-naphthylmethyl)aminobutyrate,
optically active methyl (S or R)-3-(1-phenylethyl)aminobutyrate,
optically active methyl (S or R)-3-(1-(1-naphthyl)ethyl)aminobutyrate,
optically active methyl (S or R)-3-diphenylmethylaminobutyrate,
optically active methyl (S or R)-3-benzylaminopentanoate,
optically active ethyl (S or R)-3-benzylaminopentanoate,
optically active methyl (S or R)-3-(4-chlorobenzylamino) pentanoate
optically active methyl (S or R)-3-(4-methoxybenzylamino) pentanoate,
optically active ethyl (S or R)-3-(4-nitrobenzylamino)pentanoate,
optically active methyl (S or R)-3-benzylaminohexanoate,
optically active ethyl (S or R)-3-benzylaminohexanoate,
optically active 2,2,2-trifluoroethyl (S or R)-3-benzylaminohexanoate,
optically active methyl (S or R)-3-benzylamino-4-methylpentanoate,
optically active ethyl (S or R)-3-benzylamino-4-methylpentanoate,
optically active n-octyl (S or R)-3-benzylamino-4-methylpentanoate,
optically active 2-chloroethyl (S or R)-3-benzylamino-4-methylpentanoate,
optically active 2,2,2-trichloroethyl (S or R)-3-benzylamino-4-methylpentanoate,
optically active 2,2,2-trifluoroethyl (S or R)-3-benzylamino-4-methylpentanoate,
optically active methyl (S or R)-3-(2-methylbenzyl)-4-methylpentanoate,
optically active methyl (S or R)-3-(4-methylbenzyl)-4-methylpentanoate,
optically active methyl (S or R)-3-(2-methoxybenzyl)-4-methylpentanoate,
optically active methyl (S or R)-3-(4-methoxybenzyl)amino-4-methylpentanoate,
optically active butyl (S or R)-3-(2-chlorobenzyl)amino-4-methylpentanoate,
optically active methyl (S or R)-3-(4-chlorobenzyl)amino-4-methylpentanoate,
optically active methyl (S or R)-3-(4-nitrobenzyl)amino-4-methylpentanoate,
optically active methyl (S or R)-3-(2-methoxybenzyl)amino-4-methylpentanoate,
optically active methyl (S or R)-3-(4-methoxybenzyl)amino-4-methylpentanoate,
optically active methyl (S or R)-3-(3,4-dimethoxybenzyl) amino-4-methylpentanoate,
optically active methyl (S or R)-3-(3,4-methylenedioxybenzyl)amino-4-methylpentanoate,
optically active methyl (S or R)-3-benzylamino-4-chlorobutyrate,
optically active ethyl (S or R)-3-benzylamino-4-chlorobutyrate,
optically active methyl (S or R)-3-benzylamino-4-hydroxybutyrate,
optically active methyl (S or R)-3-benzylamino-3-phenylpropionate,
optically active ethyl (S or R)-3-benzylamino-3-phenylpropionate,
optically active 2-chloroethyl (S or R)-3-benzylamino-3-phenylpropionate,
optically active 2,2,2-trichloroethyl (S or R)-3-benzylamino-3-phenylpropionate,
optically active 2,2,2-trifluoroethyl (S or R)-3-benzylamino-3-phenylpropionate,
optically active 2-cyanoethyl (S or R)-3-benzylamino-3-phenylpropionate,
optically active methyl (S or R)-3-(4-methoxybenzylamino)-3-phenylpropionate,
optically active methyl (S or R)-3-(4-hydroxybenzyl)amino-3-phenylpropionate,
optically active methyl (S or R)-3-(3,4-dimethoxybenzyl) amino-3-phenylpropionate,
optically active methyl (S or R)-3-(3,4-methylenedioxybenzyl)amino-3-phenylpropionate,
optically active methyl (S or R)-3-(1-phenylethyl)amino-3-phenylpropionate,
optically active methyl (S or R)-3-(1-(1-naphthyl)ethyl) amino-3-phenylpropionate,
optically active methyl (S or R)-3-diphenylmethylamino-3-phenylpropionate,
optically active methyl (S or R)-3-tritylamino-3-phenylpropionate,
optically active methyl (S or R)-3-benzylamino-3-(2-fluorophenyl)propionate,
optically active methyl (S or R)-3-benzylamino-3-(4-fluorophenyl)propionate, optically active ethyl (S or R)-3-benzylamino-3-(4-fluorophenyl)propionate,
optically active methyl (S or R)-3-diphenylmethylamino-3-(4-fluorophenyl)propionate,
optically active methyl (S or R)-3-benzylamino-3-(2-chlorophenyl)phenylpropionate,
optically active methyl (S or R)-3-benzylamino-3-(4-chlorophenyl)phenylpropionate,
optically active methyl (S or R)-3-benzylamino-3-(4-hydroxyphenyl)propionate,
optically active ethyl (S or R)-3-benzylamino-3-(2-hydroxyphenyl)propionate,
optically active methyl (S or R)-3-benzylamino-3-(2-methoxyphenyl)propionate,
optically active methyl (S or R)-3-benzylamino-3-(4-methoxyphenyl)propionate,
optically active ethyl (S or R)-3-benzylamino-3-(4-methoxyphenyl)propionate,
optically active methyl (S or R)-3-diphenylmethylamino-3-(4-methoxyphenyl)propionate,
optically active methyl (S or R)-3-benzylamino-3-(3,4-dimethoxyphenyl)propionate,
optically active ethyl (S or R)-3-benzylamino-3-(3,4-dimethoxyphenyl)propionate,
optically active methyl (S or R)-3-diphenylmethylamino-3-(3,4-dimethoxyphenyl)propionate,
optically active methyl (S or R)-3-benzylamino-3-(3,4-methylenedioxyphenyl)propionate,
optically active ethyl (S or R)-3-benzylamino-3-(3,4-methylenedioxyphenyl)propionate,
optically active ethyl (S or R)-3-diphenylmethylamino-3-(3,4-methylenedioxyphenyl)propionate,
optically active methyl (S or R)-3-benzylamino-3-(4-tolyl)propionate,
optically active ethyl (S or R)-3-benzylamino-3-(4-tolyl)propionate,
optically active methyl (S or R)-3-diphenylmethylamino-3-(4-tolyl)propionate,
optically active methyl (S or R)-3-benzylamino-3-(2-tolyl)propionate,
optically active methyl (S or R)-3-benzylamino-4-phenylbutyrate,
optically active methyl (S or R)-3-benzylamino-4-(4-fluorophenyl)butyrate,
optically active methyl (S or R)-3-benzylamino-4-(2-fluorophenyl)butyrate,
optically active methyl (S or R)-3-benzylamino-4-(4-chlorophenyl)butyrate,
optically active methyl (S or R)-3-benzylamino-4-(4-methoxyphenyl)butyrate,
optically active methyl (S or R)-3-benzylamino-4-(2-methoxyphenyl)butyrate,
optically active methyl (S or R)-3-benzylamino-4-(3,4-dimethoxyphenyl)butyrate,
optically active methyl (S or R)-3-benzylamino-4-(4-hydroxyphenyl)butyrate,
optically active methyl (S or R)-3-benzylamino-5-phenylpentanoate,
optically active methyl (S or R)-3-benzylamino-5-(4-fluorophenyl)pentanoate,
optically active methyl (S or R)-3-benzylamino-5-(4-chlorophenyl)pentanoate,
optically active methyl (S or R)-3-benzylamino-5-(2-fluorophenyl)pentanoate,
optically active methyl (S or R)-3-benzylamino-5-(4-methoxyphenyl)pentanoate,
optically active methyl (S or R)-3-benzylamino-5-(2-methoxyphenyl)pentanoate,
optically active methyl (S or R)-3-benzylamino-5-(3,4-dimethoxyphenyl)pentanoate,
optically active methyl (S or R)-3-benzhydrylamino-5-phenylpentanoate,
optically active methyl (S or R)-3-(1-phenylethyl)amino-4-chlorobutyrate,
optically active ethyl (S or R)-3-benzhydrylamino-4-hydroxybutyrate,
optically active methyl (S or R)-3-benzhydrylaminopentanoate,
optically active methyl (S or R)-3-(1-phenylethyl)amino-4-methylpentanoate,
optically active ethyl (S or R)-3-benzhydrylamino-4-methylpentanoate, more preferably
optically active methyl (S or R)-3-benzylaminobutyrate,
optically active ethyl (S or R)-3-benzylaminobutyrate,
optically active methyl (S or R)-3-benzylamino-3-phenylpropionate
optically active ethyl (S or R)-3-benzylamino-3-phenylpropionate
optically active methyl (S or R)-3-benzylamino-3-(4-tolyl)propionate,
optically active ethyl (S or R)-3-benzylamino-3-(4-tolyl)propionate,
optically active methyl (S or R)-3-benzylamino-3-(4-fluorophenyl)propionate
optically active methyl (S or R)-3-benzylamino-3-(3,4-methylenedioxyphenyl)propionate,
optically active ethyl (S or R)-3-benzylamino-3-(3,4-methylenedioxyphenyl)propionate,
optically active methyl (S or R)-3-benzylaminopentanoate,
optically active ethyl (S or R)-3-benzylaminopentanoate,
optically active methyl (S or R)-3-benzylaminohexanoate,
optically active ethyl (S or R)-3-benzylaminohexanoate,
optically active methyl (S or R)-3-benzylamino-4-methylpentanoate,
optically active ethyl (S or R)-3-benzylamino-4-methylpentanoate.

Also, specific examples of Compound (II-b) obtained by the hydrolysis reaction of the present invention may include, for example,
optically active (R or S) 1-benzyl-2-homopipecolic acid,
optically active (R or S) 1-(4-methylbenzyl)-2-homopipecolic acid,
optically active (R or S) 1-(hydroxybenzyl)-2-homopipecolic acid,
optically active (R or S) 1-(3,4-dihydroxybenzyl)-2-homopipecolic acid,
optically active (R or S) 1-(4-chlorobenzyl)-2-homopipecolic acid,
optically active (R or S) 1-(4-fluorobenzyl)-2-homopipecolic acid,
optically active (R or S) 1-(4-methoxybenzyl)-2-homopipecolic acid,
optically active (R or S) 1-(3,4-dimethoxybenzyl)-2-homopipecolic acid,
optically active (R or S) 1-(3,4-methylenedioxybenzyl)-2-homopipecolic acid,
optically active (R or S) 1-(4-nitrobenzyl)-2-homopipecolic acid,
optically active (R or S) 1-(1-naphthylmethyl)-2-homopipecolic acid, optically active (R or S) 1-(2-naphthylmethyl)-2-homopipecolic acid,
optically active (R or S) 1-(1-phenylethyl)-2-homopipecolic acid,
optically active (R or S) 1-(1-(2-chlorophenyl)ethyl)-2-homopipecolic acid,
optically active (R or S) 1-(1-(1-naphthyl)ethyl)-2-homopipecolic acid,
optically active (R or S) 1-diphenylmethyl-2-homopipecolic acid,
optically active (R or S) 1-trityl-2-homopipecolic acid,
optically active (R or S) 1-di(4-methoxyphenyl)methyl-2-homopipecolic acid,
and the like, preferably
optically active (R or S) 1-benzyl-2-homopipecolic acid,
optically active (R or S) 1-(4-methylbenzyl)-2-homopipecolic acid,
optically active (R or S) 1-(hydroxybenzyl)-2-homopipecolic acid,
optically active (R or S) 1-(4-chlorobenzyl)-2-homopipecolic acid,
optically active (R or S) 1-(4-methoxybenzyl)-2-homopipecolic acid,
optically active (R or S) 1-(4-nitrobenzyl)-2-homopipecolic acid,
optically active (R or S) 1-(1-naphthylmethyl)-2-homopipecolic acid,
optically active (R or S) 1-(1-phenylethyl)-2-homopipecolic acid,
optically active (R or S) 1-(1-(1-naphthyl)ethyl)-2-homopipecolic acid,
optically active (R or S) 1-diphenylmethyl-2-homopipecolic acid,
more preferably
optically active (R or S) 1-benzyl-2-homopipecolic acid,
optically active (R or S) 1-(4-methoxybenzyl)-2-homopipecolic acid,
optically active (R or S) 1-(1-phenylethyl)-2-homopipecolic acid,
optically active (R or S) 1-diphenylmethyl-2-homopipecolic acid.

Specific examples of the unreacted Compound (III-b) (having reverse steric absolute configration to that of Compound (II-b).) which was not reacted in the hydrolysis reaction of the present invention may include, for example,
optically active methyl (S or R) 1-benzyl-2-homopipecolate,
optically active ethyl (S or R) 1-benzyl-2-homopipecolate,
optically active n-butyl (S or R) 1-benzyl-2-homopipecolate,
optically active n-octyl (S or R) 1-benzyl-2-homopipecolate,
optically active 2-chloroethyl (S or R) 1-benzyl-2-homopipecolate,
optically active 2,2,2-trichloroethyl (S or R) 1-benzyl-2-homopipecolate,
optically active 2,2,2-trifluoroethyl (S or R) 1-benzyl-2-homopipecolate,
optically active 2-cyano (S or R) 1-benzyl-2-homopipecolate,
optically active methyl (S or R) 1-(4-methylbenzyl)-2-homopipecolate,
optically active ethyl (S or R) 1-(hydroxybenzyl)-2-homopipecolate,
optically active methyl (S or R) 1-(3,4-dihydroxybenzyl)-2-homopipecolate,
optically active methyl (S or R) 1-(4-chlorobenzyl)-2-homopipecolate,
optically active ethyl (S or R) 1-(4-fluorobenzyl)-2-homopipecolate,
optically active methyl (S or R) 1-(4-methoxybenzyl)-2-homopipecolate,
optically active methyl (S or R) 1-(3,4-dimethoxybenzyl)-2-homopipecolate,
optically active methyl (S or R) 1-(3,4-methylenedioxybenzyl)-2-homopipecolate,
optically active methyl (S or R) 1-(4-nitrobenzyl)-2-homopipecolate,
optically active methyl (S or R) 1-(1-naphthylmethyl)-2-homopipecolate,
optically active methyl (S or R) 1-(2-naphthylmethyl)-2-homopipecolate,
optically active methyl (S or R) 1-(1-phenylethyl)-2-homopipecolate,
optically active methyl (S or R) 1-(1-(2-chlorophenyl)ethyl)-2-homopipecolate,
optically active methyl (S or R) 1-(1-(1-naphthyl)ethyl)-2-homopipecolate,
optically active methyl (S or R) 1-diphenylmethyl-2-homopipecolate,
optically active 2,2,2-trifluoroethyl (S or R) 1-trityl-2-homopipecolate,
optically active methyl (S or R) 1-di(4-methoxyphenyl)methyl-2-homopipecolate,
and the like, preferably
optically active methyl (S or R) 1-benzyl-2-homopipecolate,
optically active ethyl (S or R) 1-benzyl-2-homopipecolate,
optically active n-octyl (S or R) 1-benzyl-2-homopipecolate,
optically active 2-chloroethyl (S or R) 1-benzyl-2-homopipecolate,
optically active 2,2,2-trichloroethyl (S or R) 1-benzyl-2-homopipecolate,
optically active 2,2,2-trifluoroethyl (S or R) 1-benzyl-2-homopipecolate,
optically active methyl (S or R) 1-(4-methylbenzyl)-2-homopipecolate,
optically active ethyl (S or R) 1-(hydroxybenzyl)-2-homopipecolate,
optically active methyl (S or R) 1-(4-chlorobenzyl)-2-homopipecolate,
optically active methyl (S or R) 1-(4-methoxybenzyl)-2-homopipecolate,
optically active methyl (S or R) 1-(4-nitrobenzyl)-2-homopipecolate,
optically active methyl (S or R) 1-(1-naphthylmethyl)-2-homopipecolate,
optically active methyl (S or R) 1-(1-phenylethyl)-2-homopipecolate,
optically active methyl (S or R) 1-(1-(1-naphthyl)ethyl)-2-homopipecolate,
optically active methyl (S or R) 1-diphenylmethyl-2-homopipecolate, more preferably
optically active methyl (S or R) 1-benzyl-2-homopipecolate,
optically active ethyl (S or R) 1-benzyl-2-homopipecolate,
optically active methyl (S or R) 1-(4-methoxybenzyl)-2-homopipecolate,
optically active methyl (S or R) 1-(1-phenylethyl)-2-homopipecolate,
optically active methyl (S or R) 1-diphenylmethyl-2-homopipecolate.

EXAMPLE

Next, the present invention is explained more specifically by referring to Examples, but the scope of the present invention is not limited by these.

Example 1

Syntheses of methyl (R)-3-benzylamino-4-methyl-pentanoate and (S)-3-benzylamino-4-methylpentanoic acid To 2 mL of a 0.1 mol/L aqueous sodium phosphate solution with a pH of 8.0 was added 100 mg of methyl (±)-3-benzylamino-4-methylpentanoate, and the mixture was maintained at 30° C. To the resulting mixture was added 1 mg of lipase (CAL; available from Roche, CHIRAZYME L-2 (trade name)) originated from *Candida antarctica* at the same temperature, and the mixture was reacted at 30° C. while stirring. After 45 minutes, at the time when the conversion rate of the starting materials reached 49.9%, 2 mol/L of hydrochloric acid was added to the reaction mixture to adjust a pH to 1, then, the mixture was filtered through Celite (No. 545), and washed with 5 ml of chloroform. To the resulting filtrate was added 20 ml of chloroform whereby the product and the starting material were extracted. The organic layer was washed with saturated brine, dried over anhydrous magnesium sulfate, and after filtration, the organic layer was concentrated under reduced pressure to obtain an oily substance. The resulting oily substance was purified by silica gel column chromatography (WAKOGEL C-200 (trade name), chloroform/methanol=98/2 to 80/20 (volume ratio)) to obtain 42.0 mg (Isolated yield based on methyl (±)-3-benzylamino-4-methylpentanoate=42.0%) of methyl (R)-3-benzylamino-4-methylpentanoate and 37.7 mg (Isolated yield based on methyl (±)-3-benzylamino-4-methylpentanoate=39.8%) of (S)-3-benzylamino-4-methylpentanoic acid.

When the optical purify of methyl (R)-3-benzylamino-4-methylpentanoate was measured by using high performance liquid chromatography that uses an optically active column, it was 99.0% ee.

When the optical purify of (S)-3-benzylamino-4-methylpentanoic acid was measured by using high performance liquid chromatography that uses an optically active column, it was 99.2% ee.

Analytical conditions of high performance liquid chromatography;
Methyl 3-benzylamino-4-methylpentanoate
Column: CHIRAL PACK AS (0.46 cmΦ×25 cm, available from DAICEL CHEMICAL INDUSTRIES, LTD.)
Solvent: hexane/isopropyl alcohol (=9/1 (volume ratio))
Flow rate: 0.5 ml/min
Temperature: 30° C.
3-Benzylamino-4-methylpentanoic acid
Column: CHIRAL CD-Ph (0.46 cmΦ×25 cm, available from SHISEIDO CO., LTD.)
Solvent: acetonitrile/water (=1/9 (volume ratio))
Potassium dihydrogen phosphate 40 mM
pH 3.5
Flow rate: 0.5 ml/min
Temperature: 25° C.

Physical properties of the methyl (R)-3-benzylamino-4-methylpentanoate were as follows.

$^1$H-NMR (δ (ppm), CDCl$_3$): 0.90 (d, 3H, J=6.8 Hz), 0.92 (d, 3H, J=6.8 Hz), 1.88 (dqq, 1H, J=4.9, 6.8, 6.8 Hz), 2.34 (dd, 1H, J=8.3, 15.1 Hz), 2.45 (dd, 1H, J=4.8, 15.1 Hz), 2.89 (ddd, 1H, J=4.8, 4.9, 8.3 Hz), 3.66 (s, 3H), 3.77 (s, 2H), 7.20-7.34 (m, 5H)
$^{13}$C-NMR (δ (ppm), CDCl$_3$): 17.5, 18.8, 21.3, 30.2, 35.5, 51.2, 51.7, 59.3, 127.2, 128.4, 139.6, 173.4, 175.9
MS (CI, i-C$_4$H$_{10}$) m/z: 236 (MH$^+$)
Elemental analysis; Calcd.: C, 71.45%; H, 9.00%; N, 5.95%. Found: C, 71.15%; H, 9.21%; N, 5.88%.

Physical properties of the (S)-3-benzylamino-4-methylpentanoic acid were as follows.

$^1$H-NMR (δ (ppm), CD$_3$OD): 0.93 (d, 3H, J=7.3 Hz), 0.95 (d, 3H, J=7.3 Hz), 2.05 (dqq, 1H, J=4.9, 7.3, 7.3 Hz), 2.31 (dd, 1H, J=8.3, 16.6 Hz), 2.41 (dd, 1H, J=3.9, 16.6 Hz), 2.88 (ddd, 1H, J=3.9, 4.9, 8.3 Hz), 4.04 (d, 1H, J=13.7 Hz), 4.12 (d, 1H, J=13.7 Hz), 7.30-7.45 (m, 5H) $^{13}$C-NMR (δ (ppm), CD$_3$OD): 16.9, 19.7, 28.3, 31.7, 47.8, 58.8, 128.6, 129.0, 129.3, 133.5, 176.0
MS (CI, i-C$_4$H$_{10}$) m/z: 222 (MH$^+$)
Elemental analysis; Calcd.: C, 70.56%; H, 8.65%; N, 6.33%. Found: C, 69.28%; H, 8.72%; N, 6.21%.

Incidentally, absolute configuration of an optically active methyl 3-benzylamino-4-methylpentanoate was determined as follows. That is, 202 mg of optically active methyl 3-benzylamino-4-methylpentanoate having an optical purity of 99.9% ee or more obtained by the same procedures as in Example 1 was dissolved in 2 mL of methanol, 22.8 mg of 20% palladium/carbon powder was added to the solution, and the mixture was reacted at room temperature while stirring. After 1 hour, the reaction mixture was filtered through Celite (No. 545), and washed with 5 ml of methanol. The resulting filtrate was concentrated under reduced pressure to obtain an oily substance. The resulting oily substance was purified by silica gel column chromatography (WAKOGEL C-200 (trade name), chloroform/methanol=98/2 to 0/100 (volume ratio)) to obtain 100 mg (Isolated yield based on optically active methyl 3-benzylamino-4-methylpentanoate=90.0%) of optically active 3-amino-4-methylpentanoic acid. Absolute configuration was determined by comparing a specific rotatory power ([α]$^{23}_D$+27.8° (C 0.20, MeOH)) of the resulting optically active 3-amino-4-methylpentanoic acid and a sign (literal value [α]$^{25}_D$−28.2° (C 0.48, MeOH)) of a specific rotatory power of (R)-3-amino-4-methylpentanoic acid described in Tetrahedron (Tetrahedron., 51 (45), 12237 (1995)).

Example 2

Syntheses of methyl (R)-3-benzylamino-4-methyl-pentanoate and (S)-3-benzylamino-4-methylpentanoic acid To a mixed solvent of 1 mL of cyclohexane and 1 mL of water was added 100 mg of methyl (±)-3-benzylamino-4-methylpentanoate, and the mixture was maintained at 30° C. To the resulting mixture was added 1 mg of lipase (CAL; available from Roche, CHIRAZYME L-2 (trade name)) originated from *Candida antarctica* at the same temperature, and the mixture was reacted at 30° C. while stirring. After 100 minutes, at the time when the conversion rate of the starting materials reached 50.0%, 2 mol/L of hydrochloric acid was added to the reaction mixture to adjust a pH to 1, filtered through Celite (No. 545), and washed with 5 ml of chloroform. To the resulting filtrate was added 20 mol of chloroform, and the product and the starting materials were extracted. The organic layer was washed with saturated brine, dried over anhydrous magnesium sulfate, and after filtration, the organic layer was concentrated under reduced pressure to obtain an oily substance. The resulting oily substance was purified by silica gel column chromatography (WAKOGEL C-200 (trade name), chloroform/methanol=98/2 to 80/20 (volume ratio)) to obtain 45.0 mg (Isolated yield based on methyl (±)-3-benzylamino-4-methylpentanoate=45.0%) of methyl (R)-3-benzylamino-4-methylpentanoate and 41.9 mg (Isolated yield based on methyl (±)-3-benzylamino-4-methylpentanoate=44.6%) of (S)-3-benzylamino-4-methylpentanoic acid.

When the optical purify of methyl (R)-3-benzylamino-4-methylpentanoate was measured by using high performance liquid chromatography that uses an optically active column, it was 99.0% ee or higher.

When the optical purify of (S)-3-benzylamino-4-methylpentanoic acid was measured by using high performance liquid chromatography that uses an optically active column, it was 99.9% ee or higher.

Analytical conditions of high performance liquid chromatography;
Methyl 3-benzylamino-4-methylpentanoate
Column: CHIRAL PACK AS (0.46 cmΦ×25 cm, available from DAICEL CHEMICAL INDUSTRIES, LTD.)
Solvent: hexane/isopropyl alcohol (=9/1 (volume ratio))
Flow rate: 0.5 ml/min
Temperature: 30° C.
3-Benzylamino-4-methylpentanoic acid
Column: CHIRAL CD-Ph (0.46 cmΦ×25 cm, available from SHISEIDO CO., LTD.)
Solvent: acetonitrile/water (=1/9 (volume ratio))
Potassium dihydrogen phosphate 40 mM
pH 3.5
Flow rate: 0.5 ml/min
Temperature: 25° C.

Incidentally, spectrum data were the same as those obtained in Example 1.

Example 3

Syntheses of methyl (R)-3-benzylamino-4-methylpentanoate and (S)-3-benzylamino-4-methylpentanoic acid To a mixed solvent of 5 mL of cyclohexane and 5 mL of water was added 1 g of methyl (±)-3-benzylamino-4-methylpentanoate, and the mixture was maintained at 30° C. To the resulting mixture was added 1 mg of lipase (CAL; available from Roche, CHIRAZYME L-2 (trade name)) originated from *Candida antarctica* at the same temperature, and the mixture was reacted at 30° C. while stirring. After 10 hours, at the time when the conversion rate of the starting materials reached 50.2%, 2 mol/L of hydrochloric acid was added to the reaction mixture to adjust a pH to 1, filtered through Celite (No. 545), and washed with 10 ml of chloroform. To the resulting filtrate was added 20 mol of chloroform, and the product and the starting materials were extracted. The organic layer was washed with saturated brine, dried over anhydrous magnesium sulfate, and after filtration, the organic layer was concentrated under reduced pressure to obtain an oily substance. The resulting oily substance was purified by silica gel column chromatography (WAKOGEL C-200 (trade name), chloroform/methanol=98/2 to 80/20 (volume ratio)) to obtain 492 mg (Isolated yield based on methyl (±)-3-benzylamino-4-methylpentanoate=49.2%) of methyl (R)-3-benzylamino-4-methylpentanoate and 443 mg (Isolated yield based on methyl (±)-3-benzylamino-4-methylpentanoate=47.1%) of (S)-3-benzylamino-4-methylpentanoic acid.

When the optical purify of methyl (R)-3-benzylamino-4-methylpentanoate was measured by using high performance liquid chromatography that uses an optically active column, it was 99.1% ee.

When the optical purify of (S)-3-benzylamino-4-methylpentanoic acid was measured by using high performance liquid chromatography that uses an optically active column, it was 98.4% ee.

Analytical conditions of high performance liquid chromatography;
Methyl 3-benzylamino-4-methylpentanoate
Column: CHIRAL PACK AS (0.46 cmΦ×25 cm, available from DAICEL CHEMICAL INDUSTRIES, LTD.)
Solvent: hexane/isopropyl alcohol (=9/1 (volume ratio))
Flow rate: 0.5 ml/min
Temperature: 30° C.
3-Benzylamino-4-methylpentanoic acid
Column: CHIRAL CD-Ph (0.46 cmΦ×25 cm, available from SHISEIDO CO., LTD.)
Solvent: acetonitrile/water (=1/9 (volume ratio))
Potassium dihydrogen phosphate 40 mM
pH 3.5
Flow rate: 0.5 ml/min
Temperature: 25° C.

Incidentally, spectrum data were the same as those obtained in Example 1.

Example 4

Syntheses of methyl (S)-3-benzylaminopentanoate and (R)-3-benzylaminopentanoic acid To 2 mL of a 0.1 mol/L aqueous sodium phosphate solution with a pH of 8.0 was added 100 mg of methyl (±)-3-benzylaminopentanoate, and the mixture was maintained at 30° C. To the resulting mixture was added 1 mg of lipase (CAL; available from Roche, CHIRAZYME L-2 (trade name)) originated from *Candida antarctica* at the same temperature, and the mixture was reacted at 30° C. while stirring. After 10 minutes, at the time when the conversion rate of the starting materials reached 47.5%, 2 mol/L of hydrochloric acid was added to the reaction mixture to adjust a pH to 1, filtered through Celite (No. 545), and washed with 5 ml of chloroform. To the resulting filtrate was added 20 mol of chloroform, and the product and the starting materials were extracted. The organic layer was washed with saturated brine, dried over anhydrous magnesium sulfate, and after filtration, the organic layer was concentrated under reduced pressure to obtain an oily substance. The resulting oily substance was purified by silica gel column chromatography (WAKOGEL C-200 (trade name), chloroform/methanol=98/2 to 80/20 (volume ratio)) to obtain 45.4 mg (Isolated yield based on methyl (±)-3-benzylaminopentanoate=45.4%) of methyl (S)-3-benzylaminopentanoate and 39.8 mg (Isolated yield based on methyl (±)-3-benzylaminopentanoate=42.5%) of (R)-3-benzylaminopentanoic acid.

When the optical purify of methyl (S)-3-benzylaminopentanoate was measured by using high performance liquid chromatography that uses an optically active column, it was 87.6% ee.

When the optical purify of (R)-3-benzylaminopentanoic acid was measured by using high performance liquid chromatography that uses an optically active column, it was 96.8% ee.

Analytical conditions of high performance liquid chromatography;
Methyl 3-benzylaminopentanoate
Column: CHIRAL PACK AS (0.46 cmΦ25 cm, available from DAICEL CHEMICAL INDUSTRIES, LTD.)
Solvent: hexane/isopropyl alcohol (=9/1 (volume ratio))
Flow rate: 0.5 ml/min
Temperature: 30° C.
3-Benzylaminopentanoic acid Column: CHIRAL CD-Ph (0.46 cmΦ×25 cm, available from SHISEIDO CO., LTD.)
Solvent: acetonitrile/water (=1/9 (volume ratio))
Potassium dihydrogen phosphate 40 mM
pH 3.5
Flow rate: 0.5 ml/min
Temperature: 25° C.

Physical properties of the methyl (S)-3-benzylaminopentanoate were as follows.

$^1$H-NMR (δ (ppm), CDCl$_3$): 0.92 (t, 3H, J=7.3 Hz), 1.53 (dq, 2H, J=5.9, 7.3 Hz), 2.44 (dd, 1H, J=6.8, 15.1 Hz), 2.48 (dd, 1H, J=5.4, 15.1 Hz), 2.97 (ddt, 1H, J=5.4, 6.8, 5.9 Hz), 3.67 (s, 3H), 3.78 (s, 2H), 7.21-7.34 (m, 5H)

$^{13}$C-NMR (δ (ppm), CDCl$_3$): 9.9, 26.9, 38.7, 51.0, 51.5, 55.5, 126.9, 128.1, 128.4, 129.0, 140.6, 173.1

MS (CI, i-C$_4$H$_{10}$) m/z: 222 (MH$^+$)

Elemental analysis; Calcd.: C, 70.56%; H, 8.65%; N, 6.33%. Found: C, 70.04%; H, 8.74%; N, 6.34%.

Physical properties of the (R)-3-benzylaminopentanoic acid were as follows.

$^1$H-NMR (δ (ppm), CD$_3$OD): 1.02 (dd, 3H, J=7.3, 7.3 Hz), 1.64 (ddq, 1H, J=7.3, 8.3, 14.7 Hz), 1.92 (ddq, 1H, J=4.4, 7.3, 14.7 Hz), 2.36 (dd, 1H, J=8.8, 17.1 Hz), 2.63 (dd, 1H, J=3.9, 17.1), 3.30 (dddd, 1H, J=3.9, 4.4, 8.3, 8.8 Hz), 4.18 (d, 1H, J=13.2 Hz), 4.24 (d, 1H, J=13.2), 7.40-7.51 (m, 5H)

$^{13}$C-NMR (δ (ppm), CD$_3$OD): 10.2, 25.0, 35.7, 58.7, 130.4, 130.5, 130.6, 133.6, 178.1

MS (CI, i-C$_4$H$_{10}$) m/z: 208 (MH$^+$)

Example 5

Syntheses of methyl (S)-3-benzylaminopentanoate and (R)-3-benzylaminopentanoic acid To a mixed solvent of 1 mL of cyclohexane and 1 mL of water was added 100 mg of methyl (±)-3-benzylaminopentanoate, and the mixture was maintained at 30° C. To the resulting mixture was added 1 mg of lipase (CAL; available from Roche, CHIRAZYME L-2 (trade name)) originated from Candida antarctica at the same temperature, and the mixture was reacted at 30° C. while stirring. After 30 minutes, at the time when the conversion rate of the starting materials reached 50.6%, 2 mol/L of hydrochloric acid was added to the reaction mixture to adjust a pH to 1, filtered through Celite (No. 545), and washed with 5 ml of chloroform. To the resulting filtrate was added 20 mol of chloroform, and the product and the starting materials were extracted. The organic layer was washed with saturated brine, dried over anhydrous magnesium sulfate, and after filtration, the organic layer was concentrated under reduced pressure to obtain an oily substance. The resulting oily substance was purified by silica gel column chromatography (WAKOGEL C-200 (trade name), chloroform/methanol=98/2 to 80/20 (volume ratio)) to obtain 46.2 mg (Isolated yield based on methyl (±)-3-benzylaminopentanoate=46.2%) of methyl (S)-3-benzylaminopentanoate and 40.3 mg (Isolated yield based on methyl (±)-3-benzylaminopentanoate=43.0%) of (R)-3-benzylaminopentanoic acid.

When the optical purify of methyl (S)-3-benzylaminopentanoate was measured by using high performance liquid chromatography that uses an optically active column, it was 98.1% ee.

When the optical purify of (R)-3-benzylaminopentanoic acid was measured by using high performance liquid chromatography that uses an optically active column, it was 95.0% ee.

Analytical conditions of high performance liquid chromatography;

Methyl 3-benzylaminopentanoate
Column: CHIRAL PACK AS (0.46 cmΦ×25 cm, available from DAICEL CHEMICAL INDUSTRIES, LTD.)
Solvent: hexane/isopropyl alcohol (=9/1 (volume ratio))
Flow rate: 0.5 ml/min
Temperature: 30° C.

3-Benzylaminopentanoic acid
Column: CHIRAL CD-Ph (0.46 cmΦ×25 cm, available from SHISEIDO CO., LTD.)
Solvent: acetonitrile/water (=1/9 (volume ratio))
Potassium dihydrogen phosphate 40 mM
pH 3.5
Flow rate: 0.5 ml/min
Temperature: 25° C.

Incidentally, spectrum data were the same as those obtained in Example 3.

Example 6

Syntheses of methyl (S)-3-benzylaminobutyrate and (R)-3-benzylaminobutyric acid

To a mixed solvent of 1 mL of cyclohexane and 1 mL of water was added 100 mg of methyl (±)-3-benzylaminobutyrate, and the mixture was maintained at 30° C. To the resulting mixture was added 0.1 mg of lipase (CAL; available from Roche, CHIRAZYME L-2 (trade name)) originated from Candida antarctica at the same temperature, and the mixture was reacted at 30° C. while stirring. After 4.5 hours, at thetime when the conversion rate of the starting materials reached 52.6%, 2 mol/L of hydrochloric acid was added to the reaction mixture to adjust a pH to 1, and 20 ml of chloroform was added to the mixture to extract the starting materials. The organic layer was washed with saturated brine, dried over anhydrous magnesium sulfate, and after filtration, the organic layer was concentrated under reduced pressure to obtain an oily substance. The resulting oily substance was purified by silica gel column chromatography (WAKOGEL C-200 (trade name), chloroform/methanol=98/2 to 80/20 (volume ratio)) to obtain 42.8 mg (Isolated yield based on methyl (±)-3-benzylaminobutyrate=42.8%) of methyl (S)-3-benzylaminobutyrate. On the other hand, the aqueous layer which contains the product was concentrated under reduced pressure to obtain an oily substance. The resulting oily substance was purified by silica gel column chromatography (WAKOGEL C-200 (trade name), chloroform/methanol=80/20 (volume ratio)) to obtain 40.0 mg (Isolated yield based on methyl (±)-3-benzylaminobutyrate=43.0%) of (R)-3-benzylaminobutyric acid.

When the optical purify of methyl (S)-3-benzylaminobutyrate was measured by using high performance liquid chromatography that uses an optically active column, it was 95.2% ee.

(R)-3-benzylaminobutyric acid was introduced into a methyl ester and when the optical purity of the resulting compound was measured by using high performance liquid chromatography that uses an optically active column, it was 85.9% ee.

Analytical conditions of high performance liquid chromatography;
Methyl 3-benzylaminobutyrate
Column: CHIRAL PACK AS (0.46 cmΦ×25 cm, available from DAICEL CHEMICAL INDUSTRIES, LTD.)
Solvent: hexane/isopropyl alcohol (=9/1 (volume ratio))
Flow rate: 0.5 ml/min
Temperature: 30° C.

Physical properties of the methyl (S)-3-benzylaminobutyrate were as follows.

$^1$H-NMR (δ (ppm), CDCl$_3$): 1.42 (d, 1H, J=6.8 Hz), 2.75 (dd, 1H, J=7.3, 17.1 Hz), 2.88 (dd, 1H, J=5.9, 17.1 Hz), 3.65 (ddd, 1H, J=5.9, 6.8, 7.3 Hz), 3.73 (s, 3H), 4.21 (d, 1H, J=14.6 Hz), 4.27 (d, 1H, J=14.6 Hz), 7.41-7.53 (m, 5H)

$^{13}$C-NMR (δ (ppm), CDCl$_3$): 20.5, 41.4, 49.7, 51.2, 51.5, 126.9, 128.1, 128.4, 140.4, 172.8

MS (CI, i-C$_4$H$_{10}$) m/z: 208 (MH$^+$)

Elemental analysis; Calcd.: C, 69.38%; H, 8.25%; N, 6.74%. Found: C, 68.74%; H, 8.23%; N, 6.76%.

Physical properties of the (R)-3-benzylaminobutyric acid were as follows.

$^1$H-NMR (δ (ppm), CD$_3$OD): 1.37 (d, 3H, J=6.4 Hz), 2.37 (dd, 1H, J=8.8, 17.1 Hz), 2.55 (dd, 1H, J=4.4, 17.1 Hz), 3.47 (ddd, 1H, J=4.4, 6.4, 8.8 Hz), 4.16 (d, 1H, J=13.2 Hz), 4.25 (d, 1H, J=13.2 Hz)

$^{13}$C-NMR (δ (ppm), CD$_3$OD): 17.1, 39.4, 53.3, 130.4, 130.5, 133.5, 177.9

MS (CI, i-C$_4$H$_{10}$) m/z: 194 (MH$^+$)

Elemental analysis; Calcd.: C, 68.37%; H, 7.82%; N, 7.25%. Found: C, 67.21%; H, 7.84%; N, 7.07%.

Example 7

Syntheses of methyl (R)-3-benzylamino-3-phenylpropionate and (S)-3-benzylamino-3-phenylpropionic acid To 10 mL of 0.1 mol/L aqueous sodium phosphate solution with a pH of 8.0 was added 1.00 g of methyl (±)-3-benzylamino-3-phenylpropionate, and the mixture was maintained at 30° C. To the resulting mixture was added 10 mg of lipase (CAL; available from Roche, CHIRAZYME L-2 (trade name)) originated from *Candida antarctica* at the same temperature, and the mixture was reacted at 30° C. while stirring. After 23 hours, at the time when the conversion rate of the starting materials reached 49.6%, 2 mol/L of hydrochloric acid was added to the reaction mixture to adjust a pH to 1, filtered through Celite (No. 545), and washed with 10 ml of chloroform 10 ml. To the resulting filtrate was added 20 mol of chloroform, and the product and the starting materials were extracted. The organic layer was washed with saturated brine, dried over anhydrous magnesium sulfate, and after filtration, the organic layer was concentrated under reduced pressure to obtain an oily substance. The resulting oily substance was purified by silica gel column chromatography (WAKOGEL C-200 (trade name), chloroform/methanol=98/2 to 80/20 (volume ratio)) to obtain 438 mg (Isolated yield based on methyl (±)-3-benzylamino-3-phenylpropionate=43.8%) of methyl (R)-3-benzylamino-3-phenylpropionate and 410 mg (Isolated yield based on methyl (±)-3-benzylamino-3-phenylpropionate=43.2%) of (S)-3-benzylamino-3-phenylpropionic acid.

When the optical purify of methyl (R)-3-benzylamino-3-phenylpropionate was measured by using high performance liquid chromatography that uses an optically active column, it was 94.2% ee.

When the optical purify of (S)-3-benzylamino-3-phenylpropionic acid was measured by using high performance liquid chromatography that uses an optically active column, it was 95.9% ee.

Analytical conditions of high performance liquid chromatography;
Methyl 3-benzylamino-3-phenylpropionate
Column: CHIRA PACK AS (0.46 cmΦ×25 cm, available from DAICEL CHEMICAL INDUSTRIES, LTD.)
Solvent: hexane/isopropyl alcohol (=9/1 (volume ratio))
Flow rate: 0.5 ml/min
Temperature: 30° C.
3-Benzylamino-3-phenylpropionic acid
Column: CHIRAL CD-Ph (0.46 cmΦ×25 cm, available from SHISEIDO CO., LTD.)
Solvent: acetonitrile/water (=1/9 (volume ratio))
Potassium dihydrogen phosphate 40 mM
pH 3.5
Flow rate: 0.5 ml/min
Temperature: 25° C.

Physical properties of the methyl (R)-3-benzylamino-3-phenylpropionate were as follows.

$^1$H-NMR (δ (ppm), CDCl$_3$): 2.62 (dd, 1H, J=5.4, 15.6 Hz), 2.72 (dd, 1H, J=8.8, 15.6 Hz), 3.53 (d, 1H, J=13.2 Hz), 3.62 (s, 3H), 3.65 (d, 1H, J=13.2 Hz), 4.11 (dd, 1H, J=5.4, 8.8 Hz), 7.21-7.35 (m, 10H)

$^{13}$C-NMR (δ (ppm), CDCl$_3$): 42.9, 51.3, 51.6, 58.8, 126.9, 127.1, 127.5, 128.1, 128.3, 128.6, 140.3, 142.5, 172.2

MS (CI, i-C$_4$H$_{10}$) m/z: 270 (MH$^+$)

Physical properties of the (S)-3-benzylamino-3-phenylpropionic acid were as follows.

$^1$H-NMR (δ (ppm), CD$_3$OD): 2.65 (dd, 1H, J=4.4, 17.1 Hz), 2.84 (dd, 1H, J=10.3, 17.1 Hz), 3.96 (d, 1H, J=13.2 Hz), 4.02 (d, 1H, J=13.2 Hz), 4.48 (dd, 1H, J=4.4, 10.3 Hz), 7.36-7.51 (m, 10H)

$^{13}$C-NMR (δ (ppm), CD$_3$OD): 40.1, 49.8, 61.2, 129.1, 130.3, 130.4, 130.5, 130.7, 133.3, 136.4, 177.3

MS (CI, i-C$_4$H$_{10}$) m/z: 256 (MH$^+$)

Example 8

Syntheses of methyl (R)-3-benzylamino-3-phenylpropionate and (S)-3-benzylamino-3-phenylpropionic acid To a mixed solvent of 1 mL of cyclohexane and 1 mL of water was added 100 mg of methyl (±)-3-benzylamino-3-phenylpropionate and the mixture was maintained at 30° C. To the resulting mixture was added 5 mg of lipase (CAL; available from Roche, CHIRAZYME L-2 (trade name)) originated from *Candida antarctica* at the same temperature, and the mixture was reacted at 30° C. while stirring. After 31 hours, at the time when the conversion rate of the starting materials reached 48.9%, 2 mol/L of hydrochloric acid was added to the reaction mixture to adjust a pH to 1, filtered through Celite (No. 545), and washed with 5 ml of chloroform. To the resulting filtrate was added 20 mol of chloroform, and the product and the starting materials were extracted. The organic layer was washed with saturated brine, dried over anhydrous magnesium sulfate, and after filtration, the organic layer was concentrated under reduced pressure to obtain an oily substance. The resulting oily substance was purified by silica gel column chromatography (WAKOGEL C-200 (trade name), chloroform/methanol=98/2 to 80/20 (volume ratio)) to obtain 41.6 mg (Isolated yield based on methyl (±)-3-benzylamino-3-phenylpropionate=41.6%) of methyl (R)-3-benzylamino-3-phenylpropionate and 40.2 mg (Isolated yield based on methyl (±)-3-benzylamino-3-phenylpropionate=42.4%) of (S)-3-benzylamino-3-phenylpropionic acid.

When the optical purify of methyl (R)-3-benzylamino-3-phenylpropionate was measured by using high performance liquid chromatography that uses an optically active column, it was 93.5% ee.

When the optical purify of (S)-3-benzylamino-3-phenylpropionic acid was measured by using high performance liquid chromatography that uses an optically active column, it was 97.9% ee.

Analytical conditions of high performance liquid chromatography;
Methyl 3-benzylamino-3-phenylpropionate
Column: CHIRAL PACK AS (0.46 cmΦ×25 cm, available from DAICEL CHEMICAL INDUSTRIES, LTD.)
Solvent: hexane/isopropyl alcohol (=9/1 (volume ratio))
Flow rate: 0.5 ml/min
Temperature: 30° C.
3-Benzylamino-3-phenylpropionic Acid
Column: CHIRAL CD-Ph (0.46 cmΦ×25 cm, available from SHISEIDO CO., LTD.)
Solvent: acetonitrile/water (=1/9 (volume ratio))
Potassium dihydrogen phosphate 40 mM
pH 3.5
Flow rate: 0.5 ml/min
Temperature: 25° C.

Incidentally, spectrum data were the same as those obtained in Example 7.

Example 9

Syntheses of methyl (R)-3-benzylamino-3-(4-fluorophenyl)propionate and (S)-3-benzylamino-3-(4-fluorophenyl)propionic acid To 2 mL of a 0.1 mol/L aqueous sodium phosphate solution with a pH of 8.0 was added 100 mg of methyl (±)-3-benzylamino-3-(4-fluorophenyl)propionate and the mixture was maintained at 30° C. To the resulting mixture was added 5 mg of lipase (CAL; available from Roche, CHIRAZYME L-2 (trade name)) originated from *Candida antarctica* at the same temperature, and the mixture was reacted at 30° C. while stirring. After 4.5 hours, at the time when the conversion rate of the starting materials reached 50.4%, 2 mol/L of hydrochloric acid was added to the reaction mixture to adjust a pH to 1, filtered through Celite (No. 545), and washed with 5 ml of chloroform. To the resulting filtrate was added 20 mol of chloroform, and the product and the starting materials were extracted. The organic layer was washed with saturated brine, dried over anhydrous magnesium sulfate, and after filtration, the organic layer was concentrated under reduced pressure to obtain an oily substance. The resulting oily substance was purified by silica gel column chromatography (WAKOGEL C-200 (trade name), chloroform/methanol=98/2 to 80/20 (volume ratio)) to obtain 40.2 mg (Isolated yield based on methyl (±)-3-benzyamino-3-(4-fluorophenyl)propionate=40.2%) of methyl (R)-3-benzylamino-3-(4-fluorophenyl)propionate and 39.9 mg (Isolated yield based on methyl (±)-3-benzylamino-3-(4-fluorophenyl)propionate=42.0%) of (S)-3-benzylamino-3-(4-fluorophenyl)propionic acid.

When the optical purify of methyl (R)-3-benzylamino-3-(4-fluorophenyl)propionate was measured by using high performance liquid chromatography that uses an optically active column, it was 91.8% ee.

When the optical purify of (S)-3-benzylamino-3-(4-fluorophenyl)propionic acid was measured by using high performance liquid chromatography that uses an optically active column, it was 90.3% ee.

Analytical conditions of high performance liquid chromatography;
Methyl 3-benzylamino-3-(4-fluorophenyl)propionate
Column: CHIRAL PACK AS (0.46 cmΦ×25 cm, available from DAICEL CHEMICAL INDUSTRIES, LTD.)
Solvent: hexane/isopropyl alcohol (=9/1 (volume ratio))
Flow rate: 0.5 ml/min
Temperature: 30° C.
3-Benzylamino-3-(4-fluorophenyl)propionic acid
Column: CHIRAL CD-Ph (0.46 cmΦ×25 cm, available from SHISEIDO CO., LTD.)
Solvent: acetonitrile/water (=1/9 (volume ratio))
Potassium dihydrogen phosphate 40 mM
pH 3.5
Flow rate: 0.5 ml/min
Temperature: 25° C.

Physical properties of the methyl (R)-3-benzylamino-3-(4-fluorophenyl)propionate are as follows.
$^1$H-NMR (δ (ppm), CDCl$_3$): 2.59 (dd, 1H, J=5.4, 15.6 Hz), 2.70 (dd, 1H, J=8.8, 15.6 Hz), 3.52 (d, 1H, J=13.2 Hz), 3.63 (s, 3H), 3.65 (d, 1H, J=13.2 Hz), 4.10 (dd, 1H, J=5.4, 8.8 Hz), 7.0-7.1 (m, 4H), 7.2-7.3 (m, 5H) $^{13}$C-NMR (δ (ppm), CDCl$_3$): 42.9, 51.3, 51.6, 58.1, 60.4, 115.3, 115.5, 127.0, 128.1, 128.2, 128.3, 128.4, 128.6, 128.7, 138.2, 140.1, 160.9, 163.4, 172.0 MS (CI, i-C$_4$H$_{10}$) m/z: 288 (MH$^+$) Elemental analysis; Calcd.: C, 71.06%; H, 6.31%; N, 4.87% Found: C, 70.69%; H, 6.42%; N, 4.86%.

Physical properties of the (S)-3-benzylamino-3-(4-fluorophenyl)propionic acid were as follows.
$^1$H-NMR (δ (ppm), CD$_3$OD): 2.65 (dd, 1H, J=4.4, 17.1 Hz), 2.82 (dd, 1H, J=10.3, 17.1 Hz), 3.95 (d, 1H, J=13.2 Hz), 4.02 (d, 1H, J=13.2 Hz), 4.50 (dd, 1H, J=4.4, 10.3 Hz), 7.19-7.25 (m, 2H), 7.36-7.45 (m, 4H), 7.49-7.52 (m, 2H) $^{13}$C-NMR (δ (ppm), CD$_3$OD): 40.2, 60.5, 117.2, 117.4, 130.3, 130.4, 130.5, 131.3, 131.4, 132.8, 133.6, 163.5, 165.9, 177.2 MS (CI, i-C$_4$H$_{10}$) m/z: 274 (MH$^+$) Elemental analysis; Calcd.: C, 70.31%; H, 5.90%; N, 5.12% Found: C, 69.44%; H, 6.08%; N, 5.04%.

Example 10

Syntheses of methyl (R)-3-benzylamino-3-(4-fluorophenyl)propionate and (S)-3-benzylamino-3-(4-fluorophenyl)propionic acid To a mixed solvent of 1 mL of cyclohexane and 1 mL of water was added 100 mg of methyl (±)-3-benzylamino-3-(4-fluorophenyl)propionate, and the mixture was maintained at 30° C. To the resulting mixture was added 5 mg of lipase (CAL; available from Roche, CHIRAZYME L-2 (trade name)) originated from *Candida antarctica* at the same temperature, and the mixture was reacted at 30° C. while stirring. After 58 hours, at the time when the conversion rate of the starting materials reached 48.0%, 2 mol/L of hydrochloric acid was added to the reaction mixture to adjust a pH to 1, filtered through Celite (No. 545), and washed with 5 ml of chloroform. To the resulting filtrate was added 20 mol of chloroform, and the product and the starting materials were extracted. The organic layer was washed with saturated brine, dried over anhydrous magnesium sulfate, and after filtration, the organic layer was concentrated under reduced pressure to obtain an oily substance. The resulting oily substance was purified by silica gel column chromatography (WAKOGEL C-200 (trade name), chloroform/methanol=98/2 to 80/20 (volume ratio)) to obtain 41.0 mg (Isolated yield based on methyl (±)-3-benzylamino-3-(4-fluorophenyl)propionate=41.0%) of methyl (R)-3-benzylamino-3-(4-fluorophenyl)propionate and 36.6 mg (Isolated yield based on methyl (±)-3-benzylamino-3-(4-fluorophenyl)propionate=38.5%) of (S)-3-benzylamino-3-(4-fluorophenyl)propionic acid.

When the optical purify of methyl (R)-3-benzylamino-3-(4-fluorophenyl)propionate was measured by using high performance liquid chromatography that uses an optically active column, it was 86.5% ee.

When the optical purify of (S)-3-benzylamino-3-(4-fluorophenyl)propionic acid was measured by using high performance liquid chromatography that uses an optically active column, it was 93.8% ee.

Analytical conditions of high performance liquid chromatography;
Methyl 3-benzylamino-3-(4-fluorophenyl)propionate
Column: CHIRAL PACK AS (0.46 cmΦ×25 cm, available from DAICEL CHEMICAL INDUSTRIES, LTD.)
Solvent: hexane/isopropyl alcohol (=9/1 (volume ratio))
Flow rate: 0.5 ml/min
Temperature: 30° C.
3-Benzylamino-3-(4-fluorophenyl)propionic acid
Column: CHIRAL CD-Ph (0.46 cmΦ×25 cm, available from SHISEIDO CO., LTD.)
Solvent: acetonitrile/water (=1/9 (volume ratio))
Potassium dihydrogen phosphate 40 mM
pH 3.5
Flow rate: 0.5 ml/min
Temperature: 25° C.

Incidentally, spectrum data were the same as those obtained in Example 9.

Example 11

Synthesis of Optically Active 3-(3-benzylamino)-3-(3,4-methylenedioxyphenyl)propionic acid To 4 mL of water were added 400 mg (1.28 mmol) of methyl (±)-3-benzylamino-3-(3,4-methylenedioxyphenyl)propionate and 107 mg (1.28 mmol) of sodium hydrogen carbonate, and the mixture was maintained to 30° C. To the resulting mixture was added 2 mg of lipase (CAL; available from Roche, CHIRAZYME L-2 (trade name)) originated from *Candida antarctica* at the same temperature, and the mixture was reacted at 30° C. while stirring. After 20 hours, at the time when the conversion rate of the starting materials reached 46.2%, 8 ml of ethyl acetate and 112 mg of sodium hydrogen carbonate were added to the reaction mixture and the aqueous layer was extracted. The resulting aqueous layer was adjusted to an inner pH of 2.0 with 2 mol/L of hydrochloric acid aqueous solution, and 8 ml of ethyl acetate and 500 mg of sodium chloride were added to the mixture to extract the organic layer. The resulting organic layer was dried over magnesium sulfate, filtered and concentrated to obtain 135 mg (Isolated yield based on methyl (±)-3-benzylamino-3-(4-fluorophenyl)propionate=35.3%) of (R) or (S)-3-benzylamino-3-(3,4-methylenedioxyphenyl)propionic acid as white crystal.

When the optical purify of 3-(R) or (S)-benzylamino-3-(3,4-methylenedioxyphenyl)propionic acid was measured by using high performance liquid chromatography that uses an optically active column, it was 97.7% ee.

Analytical conditions of high performance liquid chromatography;
3-(R) or (S)-benzylamino-3-(3,4-methylenedioxyphenyl) propionic acid
Column: CHIRAL CD-Ph (0.46 cmΦ×25 cm, available from SHISEIDO CO., LTD.)
Solvent: acetonitrile/water (=1/9 (volume ratio))
Potassium dihydrogen phosphate 40 mM
pH 3.5
Flow rate: 0.5 ml/min
Temperature: 25° C.

Physical properties of the 3-(R) or (S)-benzylamino-3-(3,4-methylenedioxyphenyl)propionic acid are as follows.
$^1$H-NMR (δ (ppm), CD$_3$OD): 2.61 (dd, 1H, J=4.4, 17.1 Hz), 2.80 (dd, 1H, J=10.3, 17.1 Hz), 3.95 (d, 1H, J=13.2 Hz), 3.99 (d, 1H, J=13.2 Hz), 4.38 (dd, 1H, J=4.4, 10.3 Hz), 4.91 (brs, 1H), 6.00 (d, 1H, J=1.5 Hz), 7.37-7.42 (m, 3H), 7.37-7.42 (m, 5H) $^{13}$C-NMR (δ (ppm), CD$_3$OD): 40.4, 61.1, 103.0, 108.8, 109.8, 123.5, 130.1, 130.3, 130.5, 133.7, 150.1, 177.5
MS (CI, i-C$_4$H$_{10}$) m/z: 300 (MH$^+$)

Example 12

Synthesis of Optically Active 3-(3-benzylamino)-3-(3,4-methylenedioxyphenyl)propionic acid To 37 mL of water were added 7.49 g (23.9 mmol) of methyl (±)-3-benzylamino-3-(3,4-methylenedioxyphenyl) propionate and 1.00 g (12.0 mmol) of sodium hydrogen carbonate, and the mixture was maintained at 30° C. To the resulting mixture was added 37.5 mg of lipase (CAL; available from Roche, CHIRAZYME L-2 (trade name)) originated from *Candida antarctica* at the same temperature, and the mixture was reacted at 30° C. while stirring. After 24 hours, at the time when the conversion rate of the starting materials reached 29.1%, 40 ml of toluene was added to the reaction mixture. After the resulting mixture was stirred for 15 minutes at room temperature, the mixture was filtered and dried to obtain 1.52 g (Isolated yield based on methyl (±)-3-benzylamino-3-(4-fluorophenyl)propionate=21.2%) of 3-(R) or (S)-benzylamino-3-(3,4-methylenedioxyphenyl)propionic acid as white crystal.

When the optical purify of 3-(R) or (S)-benzylamino-3-(3,4-methylenedioxyphenyl)propionic acid was measured by using high performance liquid chromatography that uses an optically active column, it was 99.3% ee.

Incidentally, spectrum data were the same as those obtained in Example 1.

Example 13

Synthesis of Optically Active 3-(3-benzylamino)-3-(p-tolyl)propionic Acid

To 372 mL of water were added 37.20 g (0.13 mol) of methyl (±)-3-benzylamino-3-(p-tolyl)propionate and 11.03 g (0.13 mol) of sodium hydrogen carbonate, and the mixture was maintained at 30° C. To the resulting mixture was added 186 mg of lipase (CAL; available from Roche, CHIRAZYME L-2 (trade name)) originated from *Candida antarctica* at the same temperature, and the mixture was reacted at 30° C. while stirring. After 8.5 hours, at the time when the conversion rate of the starting materials reached 39.4%, the reaction mixture was filtered to obtain a solid state product. To the resulting product was added 200 ml of toluene and the mixture was stirred at room temperature for 2 hours, then, filtered and dried to obtain 11.11 g (Isolated yield based on methyl (±)-3-benzylamino-3-(4-fluorophenyl)propionate=31.4%) of 3-(R) or (S)-benzylamino-3-(p-tolyl)propionic acid as white crystal.

When the optical purify of 3-(R) or (S)-benzylamino-3-(p-tolyl)propionic acid was measured by using high performance liquid chromatography that uses an optically active column, it was 99.3% ee.

Analytical conditions of high performance liquid chromatography;
3-(R) or (S)-benzylamino-3-(p-tolyl)propionic acid
Column: CHIRAL CD-Ph (0.46 cmΦ×25 cm, available from SHISEIDO CO., LTD.)
Solvent: acetonitrile/water (=1/9 (volume ratio))
Potassium dihydrogen phosphate 40 mM
pH 3.5
Flow rate: 0.5 ml/min
Temperature: 25° C.

Physical properties of the 3-(R) or (S)-benzylamino-3-(p-tolyl)propionic acid were as follows.
$^1$H-NMR (δ (ppm), CD$_3$OD): 2.38 (s, 3H), 2.62 (dd, 1H, J=4.4, 16.6 Hz), 2.83 (dd, 1H, J=10.3, 16.6 Hz), 3.94 (d, 1H, J=13.2 Hz), 3.99 (d, 1H, J=13.2 Hz), 4.43 (dd, 1H, J=4.4, 10.3 Hz), 4.93 (brs, 1H), 7.28-7.43 (m, 9H) $^{13}$C-NMR (δ (ppm), CD$_3$OD): 21.2, 40.2, 61.0, 129.1, 130.3, 130.4, 130.5, 131.1, 133.3, 133.4, 140.9, 177.5 MS (CI, i-C$_4$H$_{10}$) m/z: 270 (MH$^+$) Elemental analysis; Calcd.: C, 75.80%; H, 7.12%; N, 5.20% Found: C, 75.32%; H, 7.27%; N, 5.27%.

Example 14

Syntheses of methyl (S)—N-benzylhomopipecolate and (R)—N-benzylhomopipecolic acid To 1 mL of 0.1 mol/L aqueous sodium phosphate solution with a pH of 8.0 was added 50.0 mg of methyl (±)-N-benzylhomopipecolate, and the mixture was maintained at 30° C. To the resulting mixture was added 2 mg of lipase (CAL; available from Roche, CHIRAZYME L-2 (trade name)) originated from *Candida antarctica* at the same temperature, and the mixture was reacted at 30° C. while stirring. After 110 minutes, at the time when the conversion rate of the starting materials reached 41.6%, 2 mol/L of hydrochloric acid was added to the reaction mixture to adjust a pH to 1, filtered through Celite (No. 545), and washed with 5 ml of methanol. To the resulting filtrate was added 20 mol of chloroform, and the product and the starting materials were extracted. The organic layer was washed with saturated brine, dried over anhydrous magnesium sulfate, and after filtration, the organic layer was concentrated under reduced pressure to obtain an oily substance. The resulting oily substance was purified by silica gel column chromatography (WAKOGEL C-200 (trade name), chloroform/methanol=98/2 to 80/20 (volume ratio)) to obtain 18.6 mg (Isolated yield based on methyl (±)-N-benzylhomopipecolate=37.2%) of methyl (S)—N-benzylhomopipecolate and 21.7 mg (Isolated yield based on methyl (±)-N-benzylhomopipecolate=45.2%) of (R)—N-benzylhomopipecolic acid.

When the optical purify of methyl (S)—N-benzylhomopipecolate was measured by using high performance liquid chromatography that uses an optically active column, it was 68.0% ee.

When the optical purify of (R)—N-benzylhomopipecolic acid was measured by using high performance liquid chromatography that uses an optically active column, it was 95.4% ee.

Analytical conditions of high performance liquid chromatography;
Methyl N-benzylhomopipecolate
Column: CHIRAL PACK AS (0.46 cmΦ×25 cm, available from DAICEL CHEMICAL INDUSTRIES, LTD.)
Solvent: hexane/isopropyl alcohol (=9/1 (volume ratio))
Flow rate: 0.5 ml/min
Temperature: 30° C.

N-benzylhomopipecolic Acid
Column: CHIRAL CD-Ph (0.46 cmΦ×25 cm, available from SHISEIDO CO., LTD.)
Solvent: acetonitrile/water (=1/9 (volume ratio))
Potassium dihydrogen phosphate 40 mM
pH 3.5
Flow rate: 0.5 ml/min
Temperature: 25° C.

Physical properties of the methyl (S)—N-benzylhomopipecolate were as follows.
$^1$H-NMR (δ (ppm), CDCl$_3$): 1.38-1.64 (m, 6H), 2.18 (ddd, 1H, J=3.9, 7.8, 16.1 Hz), 2.45 (dd, 1H, J=7.8, 14.7 Hz), 2.62 (ddd, 1H, J=2.9, 3.9, 16.1 Hz), 2.72 (dd, 1H, J=4.9, 14.7 Hz), 2.97 (dddd, 1H, J=4.4, 4.9, 7.8, 7.8 Hz), 3.35 (d, 1H, J=13.7 Hz), 3.67 (s, 3H), 3.80 (d, 1H, J=13.7 Hz), 7.20-7.32 (m, 5H) $^{13}$C-NMR (δ (ppm), CDCl$_3$): 22.3, 25.1, 30.9, 36.4, 50.2, 51.6, 57.5, 58.5, 126.8, 128.2, 128.7, 139.6, 173.3 MS (CI, i-C$_4$H$_{10}$) m/z: 248 (MH$^+$) Elemental analysis; Calcd.: C, 72.84%; H, 8.56%; N, 5.66% Found: C, 72.50%; H, 8.73%; N, 5.66%.

Physical properties of the (R)—N-benzylhomopipecolic acid were as follows.
$^1$H-NMR (δ (ppm), CD$_3$OD): 1.55-2.15 (m, 6H), 2.96 (dd, 1H, J=6.8, 17.6 Hz), 3.03 (m, 1H), 3.22 (m, 1H), 3.14 (dd, 1H, J=4.9, 17.6 Hz), 3.71 (m, 1H), 4.27 (d, 1H, J=13.7 Hz), 4.66 (d, 1H, J=13.7 Hz), 7.46-7.59 (m, 5H) MS (CI, i-C$_4$H$_{10}$) m/z: 234 (MH$^+$)

Incidentally, absolute configuration of the optically active N-benzylhomopipecolic acid was determined as follows. That is, 100 mg of the optically active N-benzylhomopipecolic acid having an optical purity of 96.7% ee obtained by the operation of Example 1 was dissolved in 2 mL of methanol, 23.2 mg of 20% palladium/carbon powder was added to the solution, and the mixture was reacted at room temperature while stirring. After 1 hour, the reaction mixture was filtered through Celite (No. 545), and washed with 5 ml of methanol. The resulting filtrate was concentrated under reduced pressure to obtain an oily substance. This oily substance was purified by silica gel column chromatography (WAKOGEL C-200 (trade name), chloroform/methanol=98/2 to 0/100 (volume ratio)) to obtain 51.3 mg (Isolated yield based on optically active N-benzylhomopipecolic acid=85.0%) of optically active homopipecolic acid. Absolute configuration was determined by comparing the specific rotatory power ($[α]^{23}_D$–54.8° (C 1.30, H$_2$O)) of the resulting optically active homopipecolic acid and a sign (literal value $[α]^{25}_D$+22.1° (C 0.6, H$_2$O)) of the specific rotatory power of (R)-homopipecolic acid described in Synth. Comm., 7(4), 239 (1977). Example 15 Syntheses of Methyl (S)—N-benzylhomopipecolate and (R)—N-benzylhomopipecolic acid)

To a mixed solvent of 1 mL of cyclohexane and 1 mL of water was added 100 mg of methyl (±)-N-benzylhomopipecolate, and the mixture was maintained at 30° C. To the resulting mixture was added 10 mg of lipase (CAL; available from Roche, CHIRAZYME L-2 (trade name)) originated from *Candida antarctica* at the same temperature, and the mixture was reacted at 30° C. while stirring. After 7 hours, at the time when the conversion rate of the starting materials reached 50.1%, 2 mol/L of hydrochloric acid was added to the reaction mixture to adjust a pH to 1, filtered through Celite (No. 545), and washed with 5 ml of methanol. To the resulting filtrate was added 20 mol of chloroform, and the product and the starting materials were extracted. The organic layer was washed with saturated brine, dried over anhydrous magnesium sulfate, and after filtration, the organic layer was concentrated under reduced pressure to obtain an oily substance. The resulting oily substance was purified by silica gel column chromatography (WAKOGEL C-200 (trade name), chloroform/methanol=98/2 to 80/20 (volume ratio)) to obtain 42.2 mg (Isolated yield based on methyl (±)-N-benzylhomopipecolate=42.2%) of methyl (S)—N-benzylhomopipecolate and 39.7 mg (Isolated yield based on methyl (±)-N-benzylhomopipecolate=41.3%) of (R)—N-benzylhomopipecolic acid.

When the optical purify of methyl (S)—N-benzylhomopipecolate was measured by using high performance liquid chromatography that uses an optically active column, it was 99.1% ee.

When the optical purify of (R)—N-benzylhomopipecolic acid was measured by using high performance liquid chromatography that uses an optically active column, it was 98.8% ee.

Analytical conditions of high performance liquid chromatography;
Methyl N-benzylhomopipecolate
Column: CHIRAL PACK AS (0.46 cmΦ×25 cm, available from DAICEL CHEMICAL INDUSTRIES, LTD.)
Solvent: hexane/isopropyl alcohol (=9/1 (volume ratio))
Flow rate: 0.5 ml/min
Temperature: 30° C.
N-benzylhomopipecolic acid
Column: CHIRAL CD-Ph (0.46 cmΦ×25 cm, available from SHISEIDO CO., LTD.)
Solvent: acetonitrile/water (=1/9 (volume ratio))
Potassium dihydrogen phosphate 40 mM
pH 3.5
Flow rate: 0.5 ml/min
Temperature: 25° C.

Incidentally, spectrum data were the same as those obtained in Example 1.

Example 15

Syntheses of (R)—N-benzylhomopipecolic acid and methyl (S)—N-benzylhomopipecolate To a mixed solvent of 4 mL of cyclohexane and 4 mL of water was added 800 mg of methyl (±)-N-benzylhomopipecolate, and the mixture was maintained at 30° C. To the resulting mixture was added 40 mg of lipase (CAL; available from Roche, CHIRAZYME L-2 (trade name)) originated from *Candida antarctica* at the same temperature, and the mixture was reacted at 30° C. while stirring. After 5 hours, at the time when the conversion rate of the starting materials reached 49.7%, 2 mol/L of hydrochloric acid was added to the reaction mixture to adjust a pH to 1, filtered through Celite (No. 545), and washed with 5 ml of methanol. To the resulting filtrate was added 30 mol of chloroform, and the product and the starting materials were extracted. The organic layer was washed with saturated brine, dried over anhydrous magnesium sulfate, and after filtration, the organic layer was concentrated under reduced pressure to obtain an oily substance. The resulting oily substance was purified by silica gel column chromatography (WAKOGEL C-200 (trade name), chloroform/methanol=98/2 to 80/20 (volume ratio)) to obtain 359 mg (Isolated yield based on methyl (±)-N-benzylhomopipecolate=43.1%) of methyl (S)—N-benzylhomopipecolate and 314 mg (Isolated yield based on methyl (±)-N-benzylhomopipecolate=40.8%) of (R)—N-benzylhomopipecolic acid.

When the optical purify of methyl (S)—N-benzylhomopipecolate was measured by using high performance liquid chromatography that uses an optically active column, it was 95.7% ee.

When the optical purify of (R)—N-benzylhomopipecolic acid was measured by using high performance liquid chromatography that uses an optically active column, it was 96.7% ee.

Analytical conditions of high performance liquid chromatography;
Methyl N-benzylhomopipecolate
Column: CHIRAL PACK AS (0.46 cmΦ×25 cm, available from DAICEL CHEMICAL INDUSTRIES, LTD.)
Solvent: hexane/isopropyl alcohol (=9/1 (volume ratio))
Flow rate: 0.5 ml/min
Temperature: 30° C.
N-benzylhomopipecolic acid
Column: CHIRAL CD-Ph (0.46 cmΦ×25 cm, available from SHISEIDO CO., LTD.)
Solvent: acetonitrile/water (=1/9 (volume ratio))
Potassium dihydrogen phosphate 40 mM
pH 3.5
Flow rate: 0.5 ml/min
Temperature: 25° C.

Incidentally, spectrum data were the same as those obtained in Example 1.

Reference Example 1

Synthesis of methyl 3-benzylamino-4-methyl-2-pentenoate

In 140 ml of methanol was dissolved 20.00 g (0.14 mol) of methyl 3-oxo-4-methyl-pentanoate, then, 17.83 g (0.17 mol) of benzylamine and 4 g of phosphomolybdic acid were added at room temperature, and the resulting mixture was reacted under reflux and stirring for 4.5 hours. After completion of the reaction, 300 ml of toluene and 100 ml of a saturated aqueous sodium hydrogen carbonate solution were added to the reaction mixture and the organic layer was extracted. The obtained organic layer was dried over anhydrous magnesium sulfate, filtered and concentrated under reduced pressure to obtain an oily product. The obtained oily product was distilled under reduced pressure to obtain 26.36 g (Yield based on methyl 3-oxo-4-methylpentanoate=81%) of methyl 3-benzylamino-4-methyl-2-pentenoate as an objective product.

Physical properties of the methyl 3-benzylamino-4-methyl-2-pentenoate were as follows.
Boiling point: 130-133° C./188.6 Pa
(major isomer)
$^1$H-NMR (δ (ppm), CDCl$_3$): 1.11 (d, 6H, J=6.8 Hz), 3.21 (q, 1H, J=6.8 Hz), 3.64 (s, 3H), 4.46 (d, 2H, J=6.3 Hz), 4.60 (s, 1H), 7.24-7.36 (m, 5H), 9.06 (brs, 1H)
(minor isomer)
$^1$H-NMR (δ (ppm), CDCl$_3$): 1.16 (d, 3H, J=3.4 Hz), 1.19 (d, 3H, J=6.8 Hz), 2.35 (qq, 3H, J=6.8 Hz, 3.4 Hz), 3.65 (s, 3H), 4.46 (d, 2H, J=6.3 Hz), 4.83 (d, 1H, J=1.5 Hz), 7.24-7.43 (m, 5H) MS (EI) m/z: 233 (M$^+$) MS (CI, i-C$_4$H$_{10}$) m/z: 234 (MH$^+$)

Reference Example 2

Synthesis of Methyl 3-benzylamino-4-methylpentanoate

In 110 ml of acetic acid was dissolved 26.00 g (0.11 mol) of methyl 3-benzylamino-4-methyl-2-pentenoate, 5.33 g (0.14 mmol) of sodium tetrahydroborate was added to the solution at the room temperature, and the resulting mixture was reacted at the same temperature for 45 minutes under stirring. After completion of the reaction, the obtained reaction mixture was concentrated under reduced pressure, 300 ml of ethyl acetate and 100 ml of a saturated aqueous sodium hydrogen carbonate solution were added thereto, and the organic layer was adjusted to a pH of 7.2 with 1 mol/L of an aqueous sodium hydroxide solution, and the organic layer was extracted. The obtained organic layer was dried over anhydrous magnesium sulfate, and after filtration, the organic layer was concentrated under reduced pressure to obtain an oily substance. The obtained oily product was distilled under reduced pressure to obtain 21.54 g (Isolated yield based on methyl 3-benzylamino-4-methyl-2-pentenoate=82%) of methyl 3-benzylamino-4-methylpentanoate as an objective product.

Physical properties of the methyl 3-benzylamino-4-methylpentanoate were as follows.

Boiling point: 113-115° C./226.6 Pa $^1$H-NMR (δ (ppm), CDCl$_3$): 0.90 (d, 3H, J=6.8 Hz), 0.92 (d, 3H, J=6.8 Hz), 1.88 (dqq, 1H, J=4.9, 6.8, 6.8 Hz), 2.34 (dd, 1H, J=8.3, 15.1 Hz), 2.45 (dd, 1H, J=4.8, 15.1 Hz), 2.89 (ddd, 1H, J=4.8, 4.9, 8.3 Hz), 3.66 (s, 3H), 3.77 (s, 2H), 7.20-7.34 (m, 5H) $^{13}$C-NMR (δ (ppm), CDCl$_3$): 17.5, 18.8, 21.3, 30.2, 35.5, 51.2, 51.7, 59.3, 127.2, 128.4, 139.6, 173.4, 175.9 MS (CI, i-C$_4$H$_{10}$) m/z: 236 (MH$^+$) Elemental analysis; Calcd.: C, 71.45%; H, 9.00%; N, 5.95% Found: C, 71.15%; H, 9.21%; N, 5.88%.

Reference Example 3

Synthesis of N-benzyl-2-carbomethoxymethylpiperidine

In 13 ml of acetonitrile was dissolved 1.0 g (5.16 mol) of 2-carbomethoxymethylpiperidine hydrochloride, and 1.77 ml (12.72 mmol) of triethylamine and 0.76 ml (6.36 mmol) of benzyl bromide were added to the solution at room temperature, and the resulting mixture was reacted at the same temperature under stirring for 5 hours. After completion of the reaction, the obtained reaction mixture was filtered and then concentrated under reduced pressure, then, 25 ml of ethyl acetate and 15 ml of a saturated aqueous sodium hydrogen carbonate solution were added to the residue and the organic layer was extracted. The obtained organic layer was washed with 15 ml of a saturated aqueous sodium hydrogen carbonate solution, and saturated saline solution, dried over anhydrous magnesium sulfate, then, filtered and the filtrate was concentrated under reduced pressure to obtain 0.97 g of an oily substance. The resulting oily substance was purified by silica gel column chromatography (WAKOGEL C-200 (trade name), n-hexane/ethyl acetate=4/1(volume ratio)) to obtain 0.75 g (Isolated yield based on 2-carbomethoxymethylpiperidine hydrochloride=59%) of N-benzyl-2-carbomethoxymethylpiperidine.

Incidentally, the racemic 2-carboxymethylpiperidine hydrochloride used in this example was synthesized after synthesizing 2-carboxymethylpiperidine according to the method described in Can. J. Chem., 53, 41 (1975), then, subjecting to esterification reaction according to the reaction described in Can. J. Chem., 65, 2722 (1987).

Physical properties of the N-benzyl-2-carbomethoxymethylpiperidine were as follows.

$^1$H-NMR (δ (ppm), CDCl$_3$): 1.38-1.64 (m, 6H), 2.18 (ddd, 1H, J=3.9, 7.8, 16.1 Hz), 2.45 (dd, 1H, J=7.8, 14.7 Hz), 2.62 (ddd, 1H, J=2.9, 3.9, 16.1 Hz), 2.72 (dd, 1H, J=4.9, 14.7 Hz), 2.97 (dddd, 1H, J=4.4, 4.9, 7.8, 7.8 Hz), 3.35 (d, 1H, J=13.7 Hz), 3.67(s, 3H), 3.80 (d, 1H, J=13.7 Hz), 7.20-7.32 (m, 5H) $^{13}$C-NMR (δ (ppm), CDCl$_3$): 22.3, 25.1, 30.9, 36.4, 50.2, 51.6, 57.5, 58.5, 126.8, 128.2, 128.7, 139.6, 173.3 MS (EI) m/z: 247 (M$^+$)

MS (CI, i-C$_4$H$_{10}$) m/z: 248 (MH$^+$) Elemental analysis; Calcd.: C, 72.84%; H, 8.56%; N, 5.66% Found: C, 72.50%; H, 8.73%; N, 5.66%.

UTILIZABILITY IN INDUSTRY

According to the present invention, an industrially suitable process for preparing an optically active β-amino acid and an optically active β-amino acid ester or an N-substituted 2-homopipecolic acid and an optically active N-substituted 2-homopipecolic acid ester can be provided, which can give an optically active ((R) or (S))—N-substituted β-amino acid and an optically active ((S) or (R))—N-substituted β-amino acid alkyl ester or an optically active ((R) or (S))—N-substituted 2-homopipecolic acid and an optically active ((R) or (S))—N-substituted 2-homopipecolic acid ester simultaneously with a high yield and high selectivity from an N-substituted β-amino acid alkyl ester or an N-substituted 2-homopipecolic acid ester (racemic mixture) with a simple and easy process.

The invention claimed is:

1. A process for preparing an optically active β-amino acid and an optically active β-amino acid ester or N-substituted 2-homopipecolic acid and an optically active N-substituted 2-homopipecolic acid ester which comprises selectively hydrolyzing an enantiomer of a racemic mixture of an N-substituted β-amino acid alkyl ester or an N-substituted 2-homopipecolic acid ester represented by the formula (I):

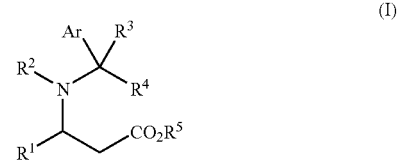

wherein Ar represents a substituted or unsubstituted aryl group, R$^1$ represents a substituted or unsubstituted alkyl group, alkenyl group, a substituted or unsubstituted aralkyl group or a substituted or unsubstituted aryl group, R$^2$ represents a hydrogen atom or R$^1$ and R$^2$ are joined covalently to form a C$_4$ saturated alkylene group, thereby forming a 6-membered ring with R$^1$ and R$^2$ and the atoms to which they are bonded, R$^3$ and R$^4$ each independently represent a hydrogen atom, a substituted or unsubstituted alkyl group or a substituted or unsubstituted aryl group, and R$^5$ represents a substituted or unsubstituted alkyl group, in the presence of a *Candida antarctica* lipase capable of catalyzing the hydrolysis of said enantiomer to form an optically active ((R) or (S))—N-substituted-β-amino acid or an optically active ((R) or (S))—N-substituted-2-homopipecolic acid represented by the formula (II):

(II)

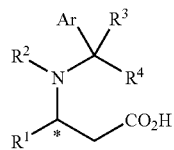

simultaneously to obtain an unreacted optically active ((S) or (R))—N-substituted-β-amino acid alkyl ester or an unreacted optically active ((S) or (R))—N-substituted-2-homopipecolic acid ester represented by the formula (III):

(III)

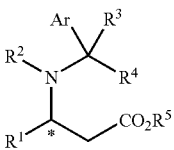

provided that the ester of formula (III) has a reverse steric absolute configuration to that of the compound represented by the formula (II).

2. The process according to claim 1, wherein the selective hydrolysis is performed in an aqueous solvent, in a buffer solvent, in a 2-phase solvent of an organic solvent and water, or in a 2-phase solvent of an organic solvent and a buffer.

3. The process according to claim 2, wherein the organic solvent is an aliphatic hydrocarbon, an aromatic hydrocarbon, an ether, or a mixed solvent thereof.

4. The process according to claim 1, wherein the compound represented by the formula (I) is a N-substituted-β-amino acid alkyl ester represented by the following formula (I-a):

(I-a)

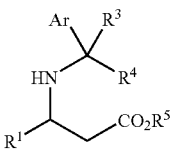

wherein Ar represents a substituted or unsubstituted aryl group, $R^1$ represents a substituted or unsubstituted alkyl group, alkenyl group, a substituted or unsubstituted aralkyl group or a substituted or unsubstituted aryl group, $R^2$ represents a hydrogen atom or $R^1$ and $R^2$ are joined covalently to form a $C_4$ saturated alkylene group, thereby forming a 6-membered ring with $R^1$ and $R^2$ and the atoms to which they are bonded, $R^3$ and $R^4$ each independently represent a hydrogen atom, a substituted or unsubstituted alkyl group or a substituted or unsubstituted aryl group, and $R^5$ represents a substituted or unsubstituted alkyl group, and wherein the compounds represented by the formula (II) and the formula (III) are an optically active ((R) or (S))—N-substituted-β-amino acid and an optically active ((S) or (R))—N-substituted-β-amino acid alkyl ester represented by the following formulae (II-a) and (III-a):

(II-a)

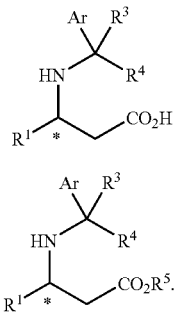

(III-a)

5. The process according to claim 1, wherein the compound represented by the formula (I) is an N-substituted-2-homopipecolic acid ester represented by the following formula (I-b):

(I-b)

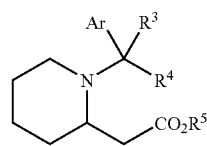

wherein Ar represents a substituted or unsubstituted aryl group, $R^3$ and $R^4$ each independently represent a hydrogen atom, a substituted or unsubstituted alkyl group or a substituted or unsubstituted aryl group, and $R^5$ represents a substituted or unsubstituted alkyl group, and wherein the compounds represented by the formula (II) and the formula (III) are an optically active ((R) or (S))—N-substituted-2-homopipecolic acid and an optically active ((S) or (R))—N-substituted-2-homopipecolic acid ester represented by the following formulae (II-b) and (III-b):

(II-b)

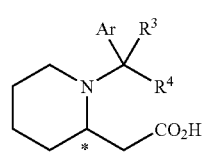

(III-b)

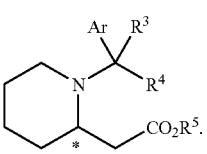

6. The process according to claim 1, wherein each of the optically active ((R) or (S))—N-substituted-β-amino acid or the optically active ((R) or (S))—N-substituted-2-homopipecolic acid represented by the formula (II):

(II)

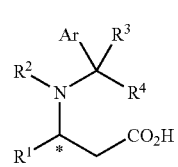

wherein Ar represents a substituted or unsubstituted aryl group, $R^1$ represents a substituted or unsubstituted alkyl group, alkenyl group, a substituted or unsubstituted aralkyl group or a substituted or unsubstituted aryl group, $R^2$ represents a hydrogen atom or wherein $R^1$ and $R^2$ are joined covalently to form a $C_4$ saturated alkylene group, thereby forming a 6-membered ring with $R^1$ and the atoms to which they are bonded, and $R^3$ and $R^4$ each independently represent a hydrogen atom, a substituted or unsubstituted alkyl group or a substituted or unsubstituted aryl group, and wherein the unreacted optically active ((S) or (R))—N-substituted-β-amino acid alkyl ester or the unreacted optically active ((S) or (R))—N-substituted-2-homopipecolic acid ester represented by the formula (III):

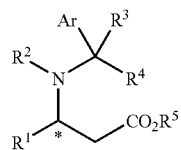

(III)

wherein $R^5$ represents a substituted or unsubstituted alkyl group, provided that the ester of formula (III) has a reverse steric absolute configuration to that of the compound represented by the formula (II), formed by hydrolysis reaction, and provided that the ester of formula (III) is isolated from the mixture thereof.

7. The preparation process according to claim 5, wherein the optically active ((R) or (S))—N-substituted-β-amino acid represented by the formula (II-a) is optically active N-substituted-β-amino acid represented by the formula (IV-a):

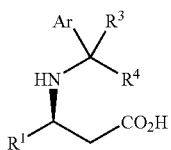

(IV-a)

wherein Ar represents a substituted or unsubstituted aryl group, and $R^3$ and $R^4$ each independently represent a hydrogen atom, a substituted or unsubstituted alkyl group or a substituted or unsubstituted aryl group, and wherein the unreacted optically active ((S) or (R))—N-substituted-β-amino acid ester is an optically active N-substituted-β-amino acid ester represented by the formula (V-a):

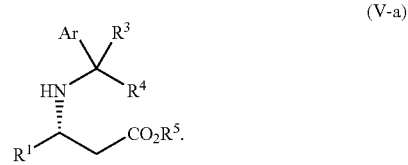

(V-a)

8. The preparation process according to claim 5, wherein the optically active ((R) or (S))—N-substituted-2-homopipecolic acid represented by the formula (II-b) is an optically active (R)—N-substituted-2-homopipecolic acid represented by the formula (IV-b):

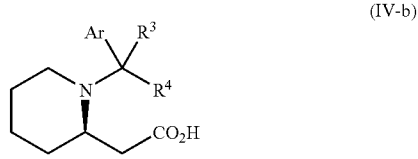

(IV-b)

wherein Ar represents a substituted or unsubstituted aryl group, and $R^3$ and $R^4$ each independently represent a hydrogen atom, a substituted or unsubstituted alkyl group or a substituted or unsubstituted aryl group, and wherein the unreacted optically active ((S) or (R))—N-substituted-2-homopipecolic acid ester represented by the formula (III-b) is an optically active (S)—N-substituted-2-homopipecolic acid ester represented by the formula (V-b):

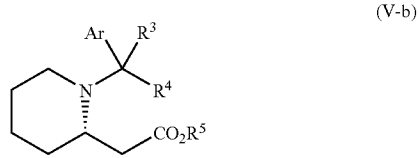

(V-b)

wherein $R^5$ represents a substituted or unsubstituted alkyl group.

* * * * *